(12) United States Patent
Bronson et al.

(10) Patent No.: US 7,632,861 B2
(45) Date of Patent: Dec. 15, 2009

(54) SUBSTITUTED HETEROCYCLIC ETHERS AND THEIR USE IN CNS DISORDERS

(75) Inventors: Joanne J. Bronson, Durham, CT (US); Andrew P. Degnan, Rocky Hill, CT (US); William D. Schmitz, Cheshire, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 12/266,627

(22) Filed: Nov. 7, 2008

(65) Prior Publication Data

US 2009/0124613 A1 May 14, 2009

Related U.S. Application Data

(60) Provisional application No. 60/987,478, filed on Nov. 13, 2007.

(51) Int. Cl.
*A61K 31/343* (2006.01)
*C07D 307/88* (2006.01)
*C07D 311/76* (2006.01)

(52) U.S. Cl. ............... 514/469; 514/450; 514/456; 549/407; 549/355; 549/467; 544/153; 546/284.1

(58) Field of Classification Search ............... 549/407, 549/355, 467; 514/450, 456, 469; 544/153; 546/284.1
See application file for complete search history.

(56) References Cited

U.S. PATENT DOCUMENTS

| | | | |
|---|---|---|---|
| 5,620,989 | A | 4/1997 | Harrison et al. |
| 5,760,018 | A | 6/1998 | Baker et al. |
| 7,098,203 | B2 | 8/2006 | Wu et al. |
| 7,138,423 | B2 | 11/2006 | Wu et al. |
| 7,276,631 | B2 | 10/2007 | Wu et al. |
| 7,494,986 | B2 | 2/2009 | Wu et al. |
| 2006/0223830 | A1 | 10/2006 | De Nanteuil et al. |
| 2007/0249607 | A1 | 10/2007 | Degnan et al. |
| 2008/0027056 | A1 | 1/2008 | Parker et al. |
| 2009/0018132 | A1 | 1/2009 | Degnan et al. |
| 2009/0018163 | A1 | 1/2009 | Schmitz et al. |

FOREIGN PATENT DOCUMENTS

| | | |
|---|---|---|
| WO | WO 03/078376 | 9/2003 |
| WO | WO 2004/004722 | 1/2004 |
| WO | WO 2004/022539 | 3/2004 |

OTHER PUBLICATIONS

Gentsch, C. et al., "Anxiolytic effect of NKP608, a NK1-receptor antagonist, in the social investigation test in gerbils", Behavioural Brain Research, vol. 133, pp. 363-368 (2002).
Kramer, M.S. et al., "Distinct Mechanism for Antidepressant Activity by Blockade of Central Substance P Receptors", Science, vol. 281, pp. 1640-1645 (1998).
Papp, M. et al., "The NK1-receptor antagonist NKP608 has an antidepressant-like effect in the chronic mild stress model of depression in rats", Behavioural Brain Research, vol. 115, pp. 19-23 (2000).
Rosen, T.J. et al., "Synthesis and Structure-Activity Relationships of CP-122,721, a Second-Generation NK-1 Receptor Antagonist", Bioorganic & Medicinal Chemistry Letters, vol. 8, pp. 281-284 (1998).
Stevenson, G.I. et al., "4,4-Disubstituted Piperidine High-Affinity $NK_1$ Antagonists: Structure-Activity Relationships and in Vivo Activity", Journal of Medicinal Chemistry, vol. 41, No. 23, pp. 4623-4635 (1998).
Stevenson, G.I. et al., "4,4-Disubstituted Piperidines: A New Class of $NK_1$ Antagonist", Journal of Medicinal Chemistry, vol. 38, No. 8, pp. 1264-1266 (1995).
Varty, G.B. et al., "The Gerbil Elevated Plus-maze II: Anxiolytic-like Effects of Selective Neurokinin NK1 Receptor Antagonists", Neuropsychopharmacology, vol. 27, No. 3, pp. 371-379 (2002).

*Primary Examiner*—Bernard Dentz
*Assistant Examiner*—David E Gallis
(74) *Attorney, Agent, or Firm*—James Epperson

(57) ABSTRACT

The invention encompasses compounds of Formula I, including pharmaceutically acceptable salts, their pharmaceutical compositions, and their use in treating CNS disorders.

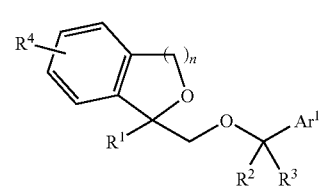

15 Claims, No Drawings

SUBSTITUTED HETEROCYCLIC ETHERS AND THEIR USE IN CNS DISORDERS

CROSS-REFERENCE TO RELATED APPLICATIONS

This application claims the benefit of U.S. Provisional Application Ser. No. 60/987,478 filed Nov. 13, 2007.

BACKGROUND OF THE INVENTION

Tachykinins are a group of naturally occurring peptides found widely distributed throughout mammals, both within the central nervous system and in the peripheral nervous and circulatory systems. The three known mammalian tachykinins are Neurokinin-1 (NK-1, substance P), Neurokinin A, and Neurokinin B. These compounds act as neurotransmitters and immunomodulators and may contribute to the pathophysiology of a wide variety of human diseases.

Receptors for tachykinins have been identified and include neurokinin-1 (NK-1 or Substance P-preferring), NK-2 (Neurokinin A-preferring) and NK-3 (Neurokinin B-preferring). NK-1 receptor antagonists are being developed for the treatment of physiological conditions associated with an excess or imbalance of tachykinins, particularly substance P. Such conditions include affective disorders such as anxiety, depression, obsessive compulsive disorder, bulimia, and panic disorder. See Gentsch et al. *Behav. Brain Res.* 2002, 133, 363; Varty et al. *Neuropsychopharmacology* 2002, 27, 371; Papp et al. *Behav. Brain Res.* 2000, 115, 19; Kramer et al. *Science* 1998, 281, 1640; and Rosen et al. *Bioorg. Med. Chem. Lett.* 1998, 8, 281. Robust antidepressant activity has been reported for two NK-1 antagonists, MK-869 (M. S. Kramer, et al., Science 1998, 281 1640) and CP-122,721 (T. J. Rosen, et al., Bioorganic and Medicinal Chemistry Letters 1998, 8, 28 and CNS Drug News, December, 2000, 24).

Selective serotonin reuptake inhibitors (SSRI's) have proven to be effective in treating depression, but have the disadvantages of delayed onset of antidepressant activity, limited efficacy, and significant side effects. See Novel strategies for pharmacotherapy of depression, K. A. Maubach, N. M. J. Rupniak, M. S. Kramer, and R. G. Hill, Current Opinion in Chemical Biology 1999, 3, 491-499. Selective serotonin reuptake inhibitors (SSRIs) in combination with other agents can be useful for the treatment of depression and other disorders and combination SERT/NK1 compounds should also be useful for these conditions. For example, the combination of SSRIs with dopamine reuptake inhibitors such bupropion and modafanil have shown clinical benefit relative to SSRIs alone, primarily due to superior side effect profiles (Bodkin et al, 1997, J Clin Psychiatry, 58: 137-145; Kennedy et al, 2002, J Clin Psychiatry, 63: 181-186). Additionally, the combination of SSRIs with 5-HT1A antagonists such as pindolol have shown improved clinical response relative to SSRIs alone (Artigas F et al, 1994, Arch Gen Psychiatry 51: 248-251; Blier P and Bergeron R, 1995, J Clin Psychopharmacol 15: 217-222). Finally, combining SSRIs with antipsychotics, such as fluoxetine plus olanzapine, has provided superior profiles in certain depressed populations including psychotic depression and bipolar depression (Corya et al, 2003, J Clin Psychiatry, 64: 1349-1356; Rothschild et al, 2004, J Clin Psychopharmacol, 24: 365-373).

NK-1 antagonists are believed to modulate 5-HT function via noradrenergic pathways and have been shown to attenuate presynaptic $5\text{-HT}_{1A}$ receptor function. NK-1 antagonists offer an alternative approach for treating depression in patients that respond poorly to the SSRI's and other available drugs and the combination of serotonin reuptake inhibition with NK-1 antagonism may lead to new classes of drugs with improved characteristics.

DESCRIPTION OF THE INVENTION

The invention encompasses compounds of Formula I, including pharmaceutically acceptable salts, their pharmaceutical compositions, and their use in treating CNS disorders.

One aspect of the invention are compounds of Formula I

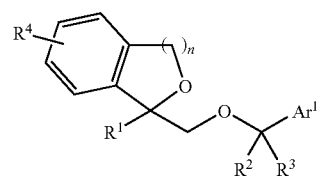

where:
$R^1$ is $(R^5R^6N)$alkyl;
$R^2$ is hydrogen or alkyl;
$R^3$ is hydrogen or alkyl;
$R^4$ is hydrogen, halo, alkyl, haloalkyl, or cyano;
$R^5$ is hydrogen or alkyl;
$R^6$ is hydrogen or alkyl;

or $R^5R^6N$ taken together is pyrrolidinyl, piperidinyl, piperazinyl, (alkyl)piperazinyl, morpholinyl, or thiomorpholinyl:
$R^7$ is hydrogen or alkyl;
$R^8$ is hydrogen or alkyl;

or $R^7R^8N$ taken together is pyrrolidinyl, piperidinyl, piperazinyl, (alkyl)piperazinyl, morpholinyl, or thiomorpholinyl:
$R^9$ is hydrogen or alkyl;
$R^{10}$ is hydrogen or alkyl;
$Ar^1$ is phenyl substituted with 0-3 substituents selected from the group consisting of halo, alkyl, haloalkyl, hydroxy, alkoxy, haloalkoxy, cyano, $NR^7R^8$, and $Ar^2$;
$Ar^2$ is phenyl or pyridinyl and is substituted with 0-3 substituents selected from the group consisting of halo, alkyl, haloalkyl, hydroxy, alkoxy, haloalkoxy, cyano, and $CONR^9R^{10}$; and
n is 1, 2, or 3;

or a pharmaceutically acceptable salt thereof.

Another aspect of the invention are compounds of Formula I where $R^1$ is $(R^5R^6N)$ethyl.

Another aspect of the invention are compounds of Formula I where $R^1$ is $(R^5R^6N)$propyl.

Another aspect of the invention are compounds of Formula I where $R^2$ and $R^3$ are hydrogen.

Another aspect of the invention are compounds of Formula I where $R^2$ is methyl and $R^3$ is hydrogen.

Another aspect of the invention are compounds of Formula I where $R^4$ is hydrogen.

Another aspect of the invention are compounds of Formula I where $R^4$ is cyano.

Another aspect of the invention are compounds of Formula I where $Ar^1$ is phenyl substituted with 2 substituents selected from the group consisting of halo, alkyl, haloalkyl, hydroxy, alkoxy, haloalkoxy, cyano, $NR^7R^8$ and $Ar^2$.

Another aspect of the invention are compounds of Formula I where $Ar^1$ is phenyl substituted with 2 substituents selected from the group consisting of halo, alkyl, haloalkyl, hydroxy, alkoxy, haloalkoxy, cyano, or $NR^7R^8$.

Another aspect of the invention are compounds of Formula I where $Ar^1$ is phenyl substituted with 1 substituent selected the group consisting of halo, alkyl, haloalkyl, hydroxy, alkoxy, haloalkoxy, cyano, and $NR^7R^8$, and is substituted with 1 $Ar^2$ substituent.

Any scope of a substituent, including $R^1$, $R^2$, $R^3$, $R^4$, $R^5$, $R^6$, $R^7$, $R^8$, $R^9$, $R^{10}$, $Ar^1$, and $Ar^2$ can be used independently with the scope of any other instance of a substituent.

Unless specified otherwise, these terms have the following meanings. "Alkyl" means a straight or branched alkyl group composed of 1 to 6 carbons. "Alkenyl" means a straight or branched alkyl group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Haloalkyl" and "haloalkoxy" include all halogenated isomers from monohalo substituted alkyl to perhalo substituted alkyl. "Aryl" includes carbocyclic and heterocyclic aromatic substituents. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some Formula I compounds contain at least one asymmetric carbon atom, an example of which is shown below. The invention includes all stereoisomeric forms of the compounds, both mixtures and separated isomers. Mixtures of stereoisomers can be separated into individual isomers by methods known in the art.

Synethic Methods

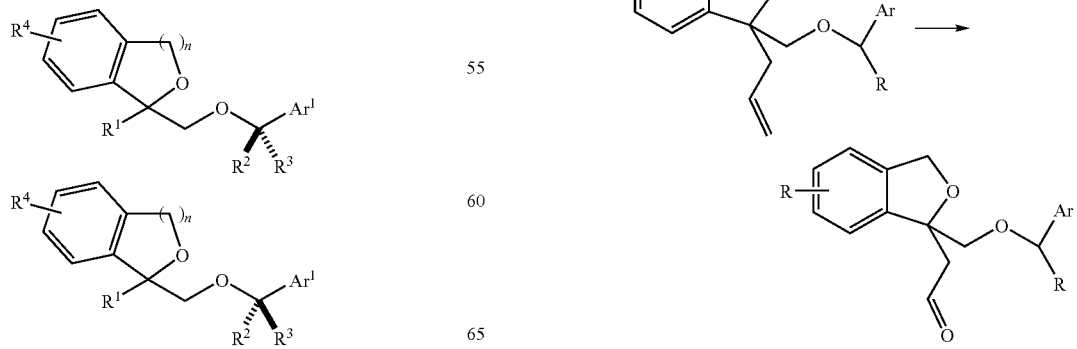

Compounds of Formula I can be made according to methods known in the art and those illustrated in the schemes below and in the specific embodiments section. The compounds can be made by reasonable variations known in the art. The variables describing general structural formulas and features in the synthetic schemes are distinct from and should not be confused with the variables in the claims or the rest of the specification. These variables are meant only to illustrate how to make some of the compounds of this invention.

Scheme 1.

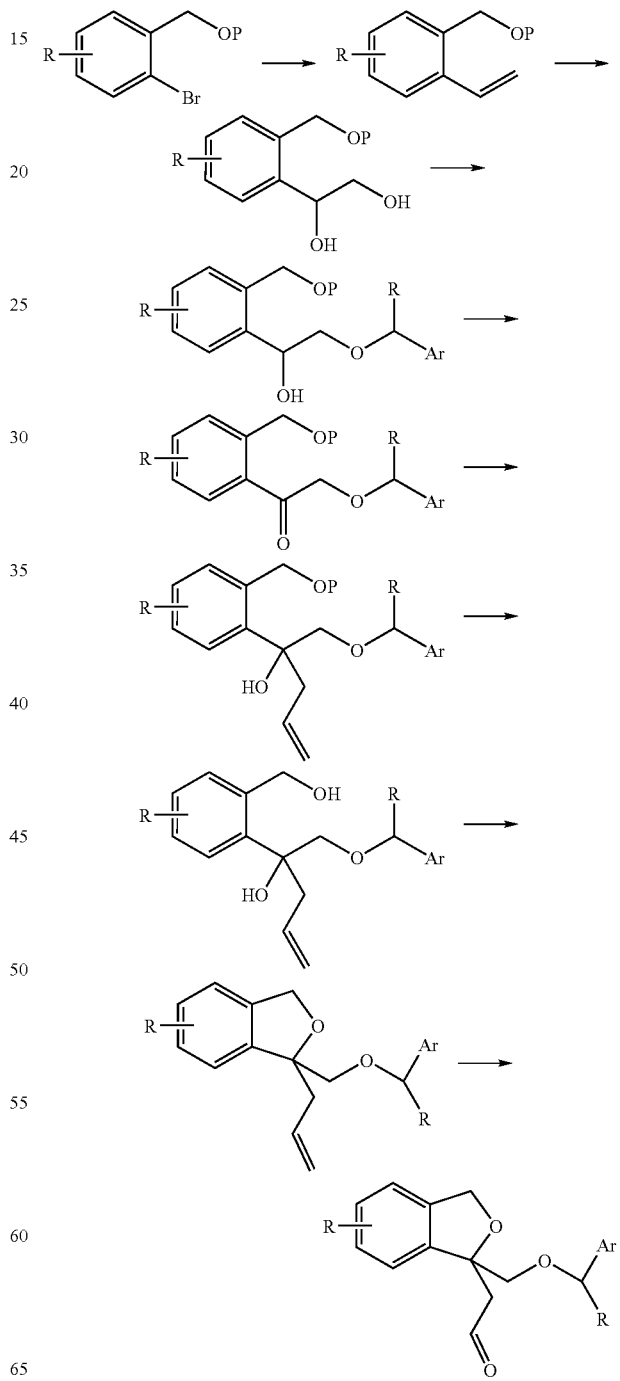

Scheme 3.
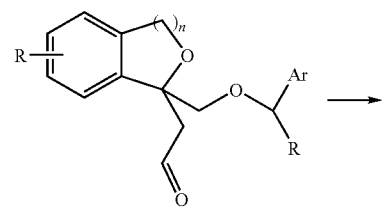
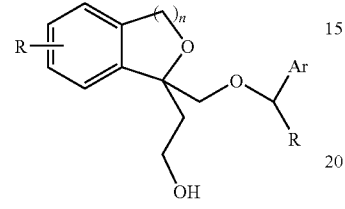
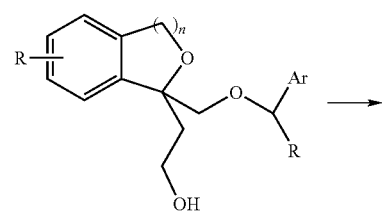
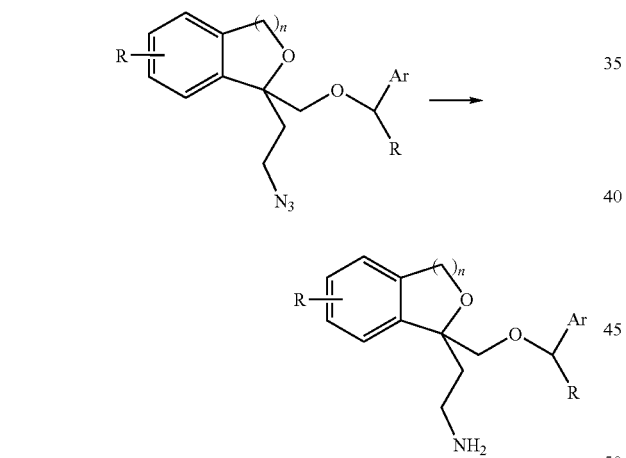
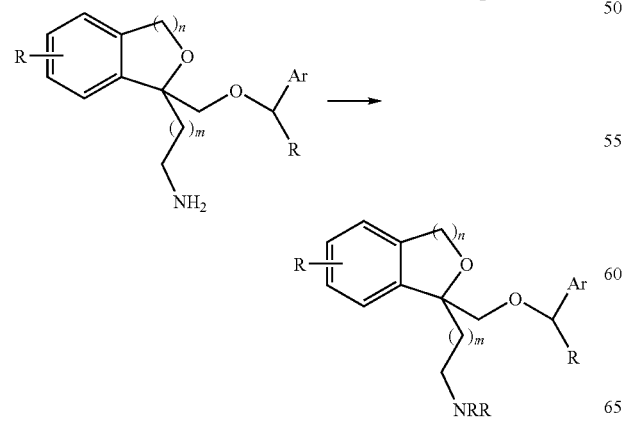
Scheme 5.
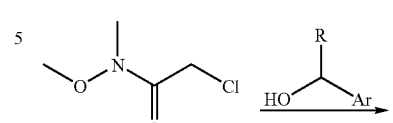
Scheme 7.

-continued

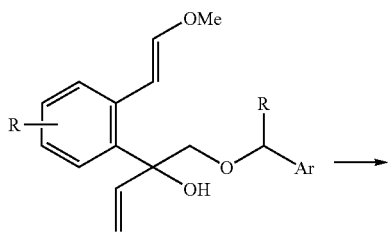

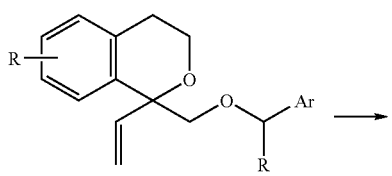

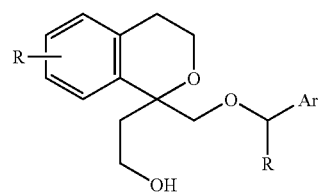

Biological Methods

NK-1 Binding assay. Crude membrane suspensions were prepared for the NK1 and SERT radioligand binding assays from U373 cells or recombinant HEK-293 cells expressing hSERT, respectively. Cells were harvested from T-175 flasks as follows. The medium is removed from the flasks and the cells rinsed with HBSS without Ca and without Mg. The cells are then incubated for 5-10 minutes in 10 mM Tris-Cl, pH 7.5, 5 mM EDTA before the cells are lifted with a combination of pipetting and scraping, as needed. To prepare membranes, the cell suspension is collected into centrifuge bottles and homogenized for 30 seconds with a Polytron homogenizer. The suspension is centrifuged for 30 min @ 32,000×g, 4° C., then the supernatant is decanted and the pellet resuspended and homogenized in 50 mM Tris-Cl, pH 7.5, 1 mM EDTA for 10 seconds. The suspension is then centrifuged again for 30 min @ 32,000×g, 4° C. The supernatant is decanted and the pellet resuspended in 50 mM Tris-Cl, pH 7.5, 1 mM EDTA and briefly homogenized. A Bradford assay (Bio-rad) is performed and the membrane preparation diluted to 2 mg/ml with 50 mM Tris-Cl, pH 7.5, 1 mM EDTA. Aliquots are prepared, and then frozen and stored at −80° C.

NK1 radioligand binding assay. Compounds are dissolved in 100% DMSO at a concentration 100× the desired highest assay concentration, serially diluted 1:3 in 100% DMSO, and 0.6 ul/well of each solution is dispensed to a Nunc polypropylene, round bottom, 384 well plate. 100% inhibition is defined with 0.6 ul/well of 1 mM L-733,060 (Sigma L-137) dissolved in DMSO. 30 ul/well of a 2×U373 membrane preparation (267 ug/ml in 100 mM Tris-Cl, pH 7.5, 6 mM $MgCl_2$, 0.2% (v/v) Sigma mammalian protease inhibitor cocktail (Sigma P-8340), and 4 ug/ml chymostatin, Sigma C-7268) and 30 ul/well of a 2×radioligand solution (400 pM [$^{125}$I]Substance P (Perkin Elmer NEX-190) in 1% (w/v) BSA (Sigma A-2153), 0.1 mg/ml bacitracin, Sigma B-0125) are added to the well and the reaction incubated for 1 hour at room temperature. The contents of the assay plate are then transferred to a Millipore Multiscreen$_{HTS}$ GF/B filter plate which has been pretreated with 0.5% PEI for at least one hour. The plate is vacuum filtered and washed with 7 washes of 100 ul/well of 20 mM Tris-Cl, pH 7.5, 0.5% (w/v) BSA chilled to 4° C. The filtration and washing is completed in less than 90 s. The plates are air-dried overnight, 12 ul/well of MicroScint scintillation fluid added, and the plates counted in a Trilux.

SERT radioligand binding assay. Compounds are dissolved in 100% DMSO at a concentration 100× the desired highest assay concentration, serially diluted 1:3 in 100% DMSO, and 0.4 ul/well of each solution is dispensed to a Nunc polypropylene, round bottom, 384 well plate. 100% inhibition is defined with 0.4 ul/well of 1 mM fluoxetine (Sigma F-132) dissolved in DMSO. 20 ul/well of a 2×HEK-hSERT membrane preparation (15 ug/ml in 50 mM Tris-Cl, pH 7.5, 120 mM NaCl, 5 mM KCl) and 20 ul/well of a 2×radioligand solution (520 pM [$^{125}$I]RTI-55 (Perkin-Elmer NEX-272) in 50 mM Tris-Cl, pH 7.5, 120 mM NaCl, 5 mM KCl) are added to each well and the reaction incubated for 1 hour at room temperature. The contents of the assay plate are then transferred to a Millipore Multiscreen$_{HTS}$ GF/B filter plate which has been pretreated with 0.5% PEI for at least one hour. The plate is vacuum filtered and washed with 7 washes of 100 ul/well of 50 mM Tris-Cl, pH 7.5, 120 mM NaCl, 5 mM KCl chilled to 4° C. The filtration and washing is completed in less than 90 s. The plates are air-dried overnight, 12 ul/well of MicroScint scintillation fluid added, and the plates counted in a Trilux.

Data analysis. The raw data are normalized to percent inhibition using control wells defining 0% (DMSO only) and 100% (selective inhibitor) inhibition which are run on each plate. Each plate is run in triplicate, and the concentration response curve thus generated is fit using the four-parameter dose response equation, $Y = Bottom + (Top-Bottom)/(1+10^{((LogIC_{50}-X)*HillSlope)})$ in order to determine the $IC_{50}$ value for each compound. The radioligand concentration chosen for each assay corresponds to the $K_d$ concentration determined through saturation binding analysis for each assay. NK-1 and serotonin transporter binding results are shown in Table 1.

TABLE 1
| Example | Structure | NK-1 IC$_{50}$ (nM) | SERT IC$_{50}$ (nM) |
|---|---|---|---|
| 1 | 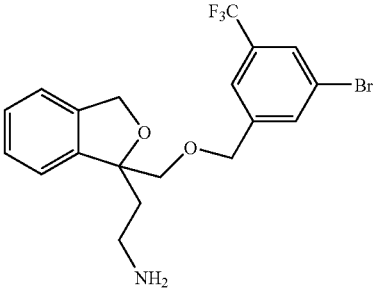 | A | A |
| 2 | 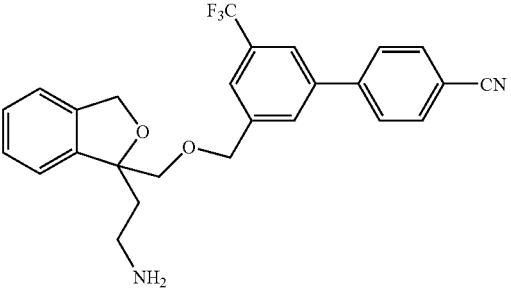 | A | B |
| 3 | 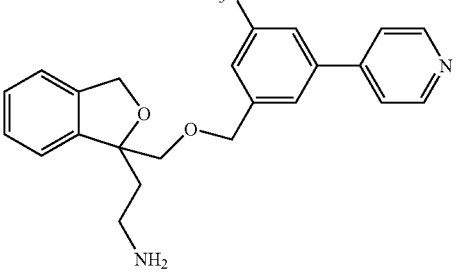 | A | B |
| 4 | 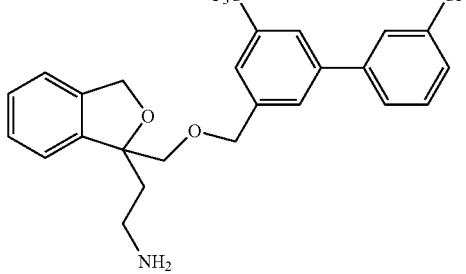 | B | B |
| 5 | 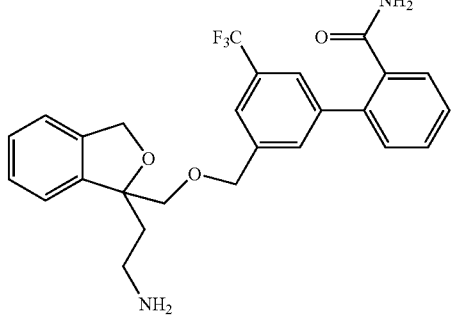 | C | C |

TABLE 1-continued
| Example | Structure | NK-1 IC$_{50}$ (nM) | SERT IC$_{50}$ (nM) |
|---------|-----------|---------------------|---------------------|
| 6 | 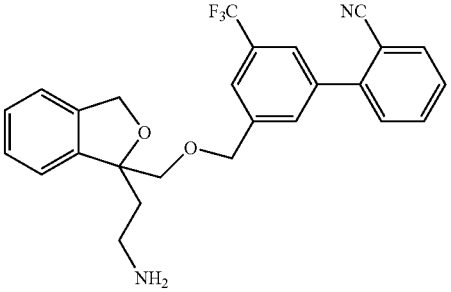 | B | B |
| 7 | 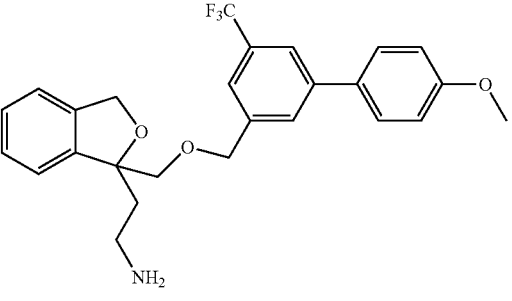 | A | C |
| 8 | 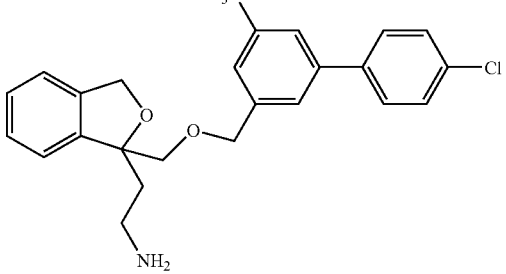 | A | B |
| 9 | 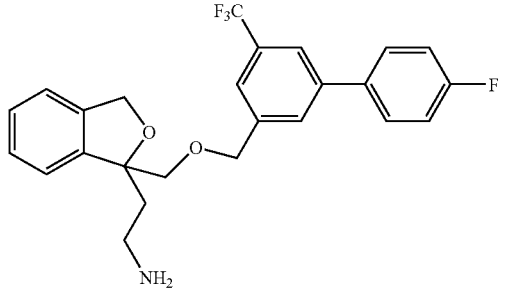 | A | B |
| 10 | 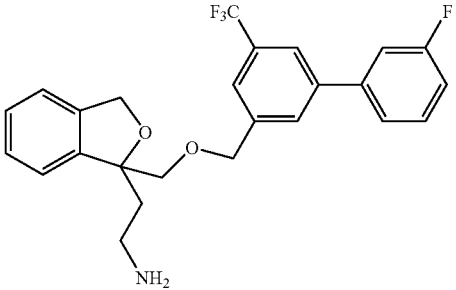 | A | B |

TABLE 1-continued
| Example | Structure | NK-1 IC$_{50}$ (nM) | SERT IC$_{50}$ (nM) |
|---|---|---|---|
| 11 | 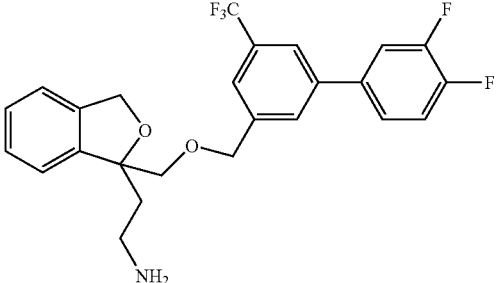 | A | B |
| 12 | 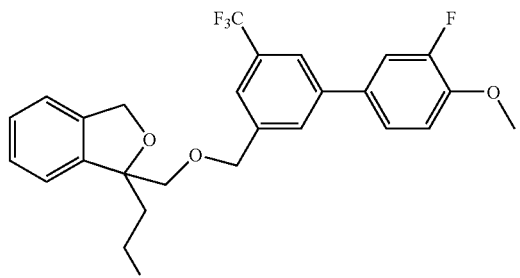 | A | C |
| 13 | 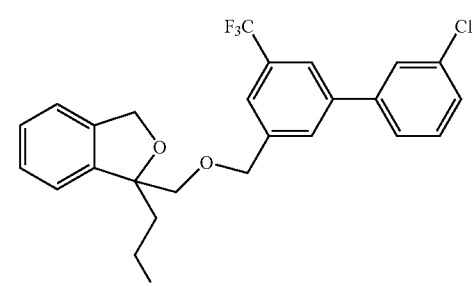 | B | C |
| 14 | 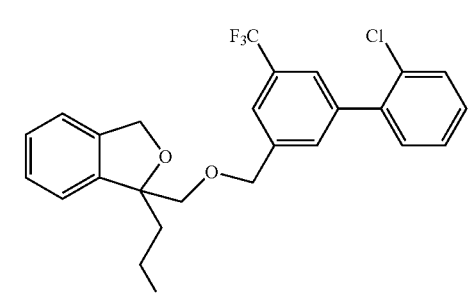 | B | C |
| 15 | 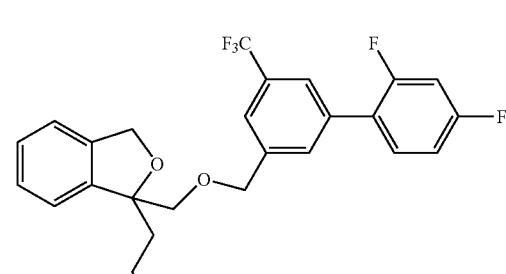 | A | B |

TABLE 1-continued
| Example | Structure | NK-1 IC$_{50}$ (nM) | SERT IC$_{50}$ (nM) |
| --- | --- | --- | --- |
| 16 | 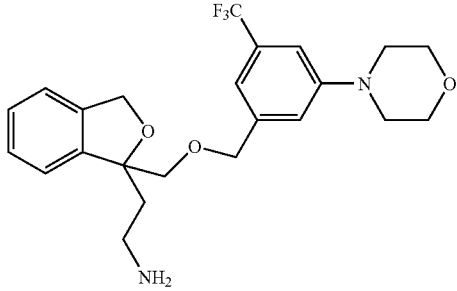 | A | C |
| 17 | 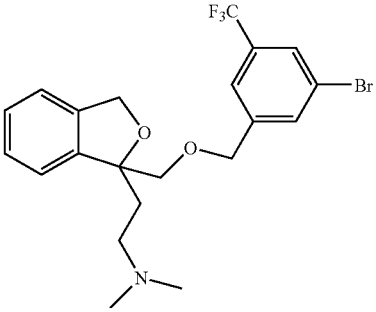 | A | A |
| 18 | 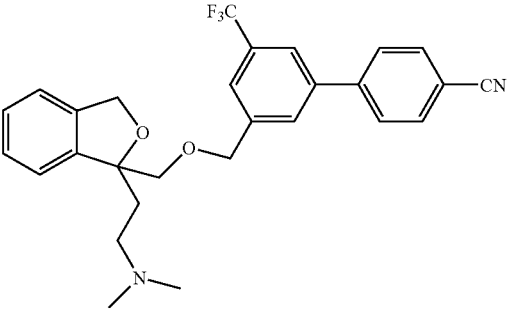 | A | B |
| 19 | 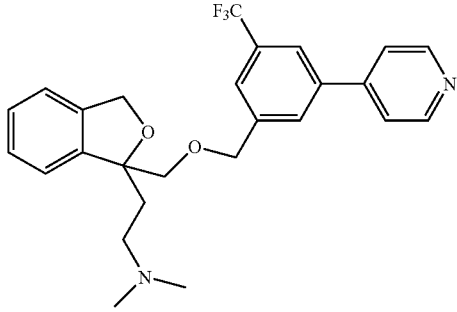 | A | A |
| 20 | 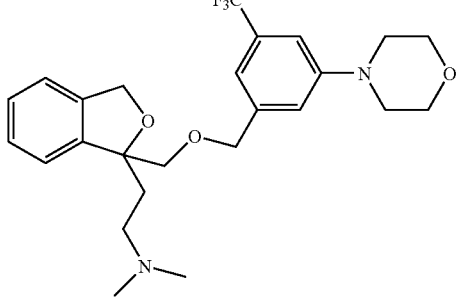 | A | A |

TABLE 1-continued

| Example | Structure | NK-1 IC$_{50}$ (nM) | SERT IC$_{50}$ (nM) |
| --- | --- | --- | --- |
| 21 | 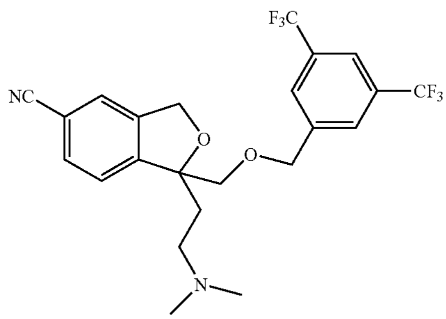 | A | C |
| 22 | 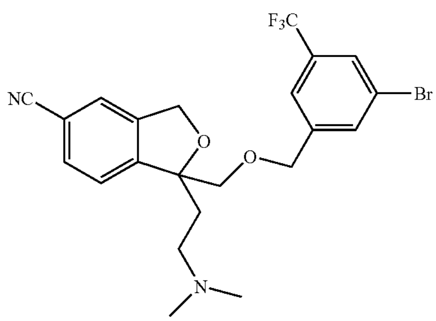 | A | C |
| 23 | 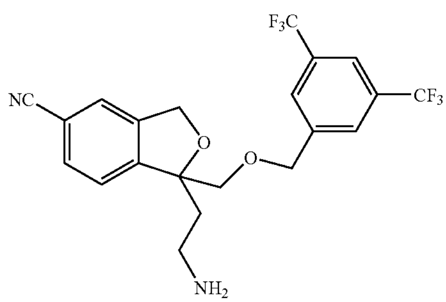 | A | B |
| 24 | 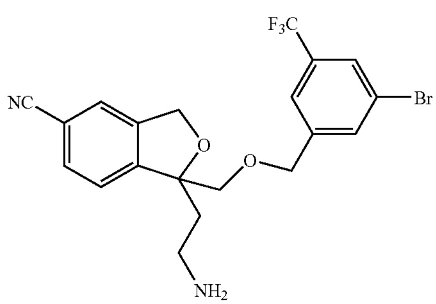 | A | A |
| 25 | 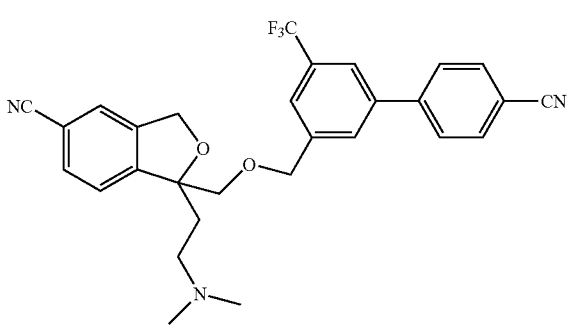 | A | C |

TABLE 1-continued
| Example | Structure | NK-1 IC$_{50}$ (nM) | SERT IC$_{50}$ (nM) |
|---|---|---|---|
| 26 | 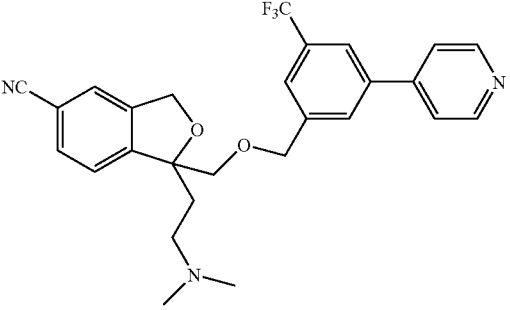 | B | C |
| 27 | 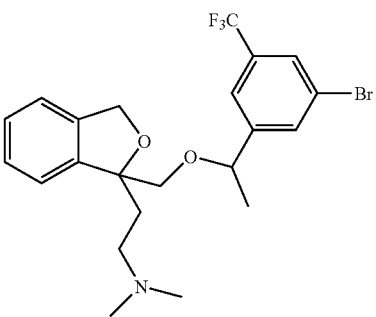 | A | B |
| 28 | 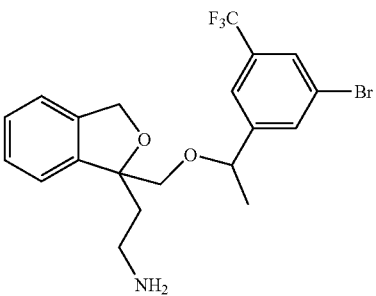 | A | C |
| 29 | 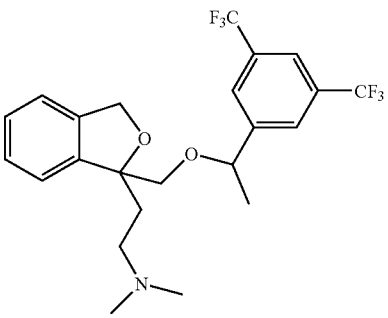 | A | C |
| 30 | 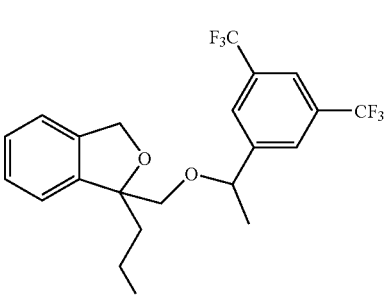 | A | C |

TABLE 1-continued
| Example | Structure | NK-1 IC$_{50}$ (nM) | SERT IC$_{50}$ (nM) |
| --- | --- | --- | --- |
| 31 | 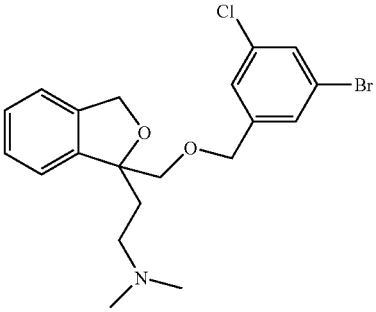 | B | A |
| 32 | 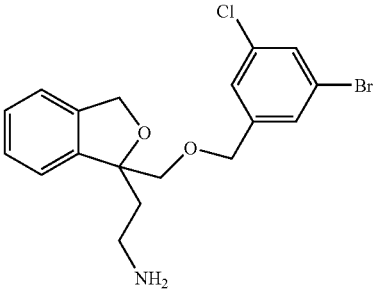 | A | A |
| 33 | 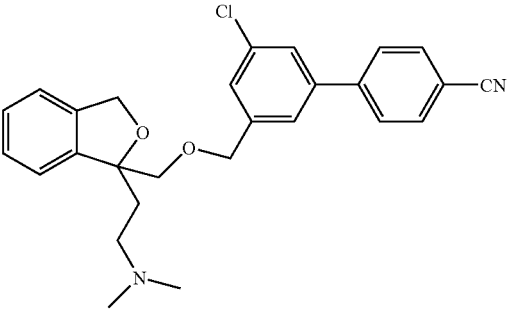 | A | A |
| 34 | 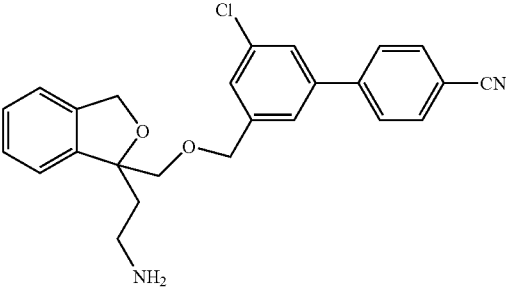 | A | A |
| 35 | 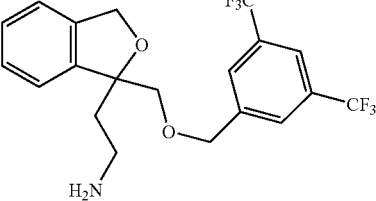 | A | B |

TABLE 1-continued

| Example | Structure | NK-1 IC$_{50}$ (nM) | SERT IC$_{50}$ (nM) |
|---|---|---|---|
| 36 | 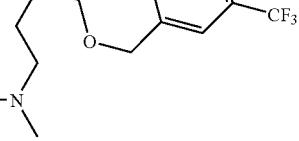 | A | A |
| 37 | 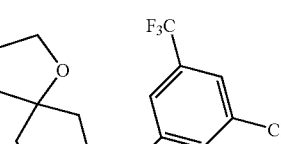 | A | A |
| 38 | 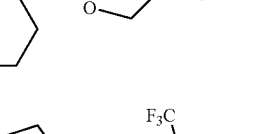 | A | C |
| 39 | 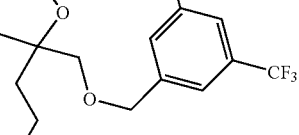 | A | A |
| 40 | 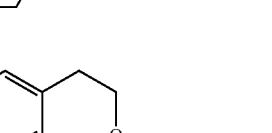 | A | A |

Values: A = 0.01-100 nM; B = 100-300 nM; C > 300 nM.

Pharmaceutical Composition and Methods of Use

The compounds of Formula I demonstrate inhibition of neurokinin-1 or serotonin reuptake or both. Inhibition of these receptors correlates with efficacy for affective disorders such as anxiety, depression, obsessive compulsive disorder, bulimia, and panic disorder. As such, the compounds of Formula I can be useful for the treatment of these disorders and other aspects of the invention are compositions and methods of using the compounds to treat these conditions and other conditions associated with aberrant levels of tachykinins or serotonin or both.

The compounds of this invention are generally given as pharmaceutical compositions comprised of a therapeutically effective amount of a compound of Formula I, or a pharmaceutically acceptable salt, and a pharmaceutically acceptable carrier and may contain conventional excipients. A therapeutically effective amount is the amount needed to provide a meaningful patient benefit as determined by practitioners in that art. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Compositions are made using common formulation techniques and conventional excipients (such as binding and wetting agents) and vehicles (such as water and alcohols).

Solid compositions are normally formulated in dosage units providing from about 1 to about 1000 mg of the active ingredient per dose. Some examples of solid dosage units are 1 mg, 10 mg, 100 mg, 250 mg, 500 mg, and 1000 mg. Liquid compositions are generally in a unit dosage range of 1-100 mg/mL. Some examples of liquid dosage units are 1 mg/mL, 10 mg/mL, 25 mg/mL, 50 mg/mL, and 100 mg/mL. Generally, the dosage unit will be in a unit range similar to agents of that class used clinically, for example fluoxetine.

The invention encompasses all conventional modes of administration; oral and parenteral methods are preferred. Generally, the dosing regimen will be similar to agents of that class used clinically, for example fluoxetine. Typically, the daily dose will be 0.01-100 mg/kg body weight daily. Generally, more compound is required orally and less parenterally. The specific dosing regime, however, should be determined by a physician using sound medical judgement.

Tachykinin and serotonin modulators are associated with depression. Accordingly, another aspect of the invention are methods for treating depressive disorders including Major Depressive Disorders (MDD), bipolar depression, unipolar depression, single or recurrent major depressive episodes, recurrent brief depression, catatonic features, melancholic features including feeding disorders, such as anorexia, weight loss, atypical features, anxious depression, or postpartum onset. Other central nervous system disorders encompassed within the term MDD include neurotic depression, post-traumatic stress disorders (PTSD) and social phobia, with early or late onset dementia of the Alzheimer's type, with depressed mood, vascular dementia with depressed mood, mood disorders and tolerance induced by drugs such as alcohol, amphetamines, cocaine, inhalants, opioids, sedatives, anxiolytics and other substances, schizoaffective disorder of the depressed type, and adjustment disorder with depressed mood.

Tachykinin and serotonin modulators are also associated with the treatment or prevention of schizophrenic disorders. Accordingly, another aspect of the invention are methods for treating schizophrenic disorders including paranoid schizophrenia, disorganized schizophrenia, catatonic schizophrenia, undifferentiated schizophrenia, residual schizophrenia.

Tachykinin and serotonin modulators are also associated with the treatment or prevention of anxiety. Accordingly, another aspect of the invention are methods for treating anxiety disorders including panic disorders, agoraphobia, phobias, obsessive-compulsive disorder, stress disorders including post-traumatic stress disorders, generalized anxiety disorders, acute stress disorders and mixed anxiety-depression disorders.

Tachykinin and serotonin modulators are also associated with the treatment or prevention of cognitive disorders. Accordingly, another aspect of the invention are methods for treating cognitive disorders including dementia, and amnesia disorders. Tachykinin and serotonin modulators are also associated with the treatment or prevention of memory and cognition in healthy humans.

Tachykinin and serotonin modulators are also associated with use as analgesics. Accordingly, another aspect of the invention are methods for treating pain, including the treatment of traumatic pain such as postoperative pain, chronic pain such as arthritic pain such as occurring in osteo-, rheumatoid or psoriatic arthritis, neuropathic pain such as postherpetic neuralgia, trigeminal neuralgia, segmental or intercostal neuralgia, fibromyalgia, peripheral neuropathy, diabetic neuropathy, chemotherapy-induced neuropathy, AIDS-related neuropathy, various forms of headache such as migraine, acute or chronic tension headache, cluster headaches, maxillary sinus pain, cancer pain, pain of bodily origin, gastrointestinal pain, sport's injury pain, dysmennorrhoea, menstrual pain, meningitis, musculoskeletal pain, low back pain e.g. spinal stenosis, prolapsed disc, sciatica, angina, ankylosing spondyolitis, gout, burns, scar pain, itch and thalamic pain such as post stroke thalamic pain.

Tachykinin and serotonin modulators are also associated with the treatment or prevention of sleep disorders. Accordingly, another aspect of the invention are methods for treating sleep disorders including insomnia, sleep apnea, narcolepsy, and circadian rhymic disorders.

Tachykinin and serotonin modulators are also associated with the treatment or prevention of inflammation. Accordingly, another aspect of the invention are methods for treating inflammation, including the treatment of inflammation in asthma, influenza and chronic bronchitis, in the treatment of inflammatory diseases of the gastrointestinal tract such as Crohn's disease, ulcerative colitis, inflammatory bowel disease and non-steroidal anti-inflammatory drug induced damage, inflammatory diseases of the skin such as herpes and eczema, inflammatory diseases of the bladder such as cystitis and urge incontinence, and eye and dental inflammation.

Tachykinin and serotonin modulators are also associated with the treatment or prevention of allergic disorders. Accordingly, another aspect of the invention are methods for treating allergic disorders, in particular allergic disorders of the skin such as urticaria, and allergic disorders of the airways such as rhinitis.

Tachykinin and serotonin modulators are also associated with the treatment or prevention of emesis, nausea, retching and vomiting. Accordingly, another aspect of the invention are methods for treating these disorders.

Tachykinin and serotonin modulators are also associated with the treatment or prevention of premenstrual dysphoric disorder (PMDD), in chronic fatigue syndrome and multiple sclerosis. Accordingly, another aspect of the invention are methods for treating these disorders.

DESCRIPTION OF SPECIFIC EMBODIMENTS

The following experimental procedures describe the synthesis of some Formula I compounds. Standard chemistry conventions are used in the text unless otherwise noted. The experimental encompass reasonable variations known in the art.

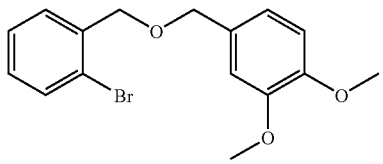

Intermediate 1

4-((2-bromobenzyloxy)methyl)-1,2-dimethoxybenzene. To a stirred solution of 3,4-dimethoxybenzyl alcohol (6.10 mL, 42 mmol) in dry DMF (100 mL) cooled to 0° C., was added 60 wt. % sodium hydride (3.12 g, 78 mmol). After 30 minutes, 2-bromobenzyl bromide (10 g, 40 mmol) was added as a solid. Stirring was continued at 0° C. for 3 hours. The reaction was quenched by slow addition of saturated NH$_4$Cl and extracted with (3×100 mL) EtOAc. The combined organics were washed with brine, dried over MgSO$_4$ and concentrated under vacuum. Column chromatography on silica gel (10-30% ethyl acetate/hexanes) afforded intermediate 1 (14.16 g, 41.9 mmol, 90%). $^1$H NMR (500 MHz, CHLOROFORM-D) δ ppm 3.88 (d, J=5.19 Hz, 6H) 4.58 (d, J=18.31 Hz, 4H) 6.79-6.87 (m, 1H) 6.89-6.94 (m, 1H) 6.95 (d, J=1.83 Hz, 1H) 7.08-7.17 (m, 1H) 7.31 (t, J=7.17 Hz, 1H) 7.50 (d, J=7.02 Hz, 1H) 7.53 (d, J=7.93 Hz, 1H). Mass spec.: 338.21 (MH)$^+$.

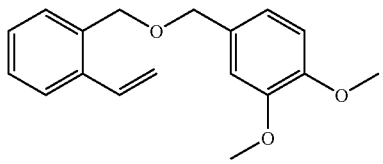

Intermediate 2

1,2-dimethoxy-4-((2-vinylbenzyloxy)methyl)benzene. To a stirred solution of 4-((2-bromobenzyloxy)methyl)-1,2-dimethoxybenzene (10 g, 29.6 mmol) in isopropanol (120 mL), was added triethylamine (14.46 mL, 103 mmol), potassium vinyltrifluoroborate (3.97 g, 29.6 mmol), and 1,1'-bis(diphenylphosphino)ferrocene palladium (II) chloride (1.22 g, 1.48 mmol). The resulting mixture was heated in a microwave reactor at 130° C. for 30 minutes then cooled, filtered through a pad of celite and evaporated under vacuum. Column chromatography on silica gel (10-30% ethyl acetate/hexanes) afforded intermediate 2 (5.94 g, 20.8 mmol, 70%). $^1$H NMR (500 MHz, CHLOROFORM-D) δ ppm 3.87 (s, 6H) 4.49 (s, 2H) 4.57 (s, 2H) 5.26-5.33 (m, 1H) 5.67 (dd, J=17.40, 1.22 Hz, 1H) 6.81-6.85 (m, 1H) 6.86-6.93 (m, 2H) 7.02 (dd, J=17.40, 10.99 Hz, 1H) 7.22-7.37 (m, 2H) 7.54 (d, J=7.32 Hz, 1H). Mass spec.: 285.35 (MH)$^+$.

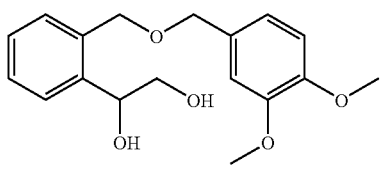

Intermediate 3

1-(2-((3,4-dimethoxybenzyloxy)methyl)phenyl)ethane-1,2-diol. To a stirred solution of 1,2-dimethoxy-4-((2-vinylbenzyloxy)methyl)benzene (5.94 g, 20.9 mmol), was added osmium tetroxide 2.5 wt. % solution in 2-methyl-2-propanol (10.62 mL, 1.04 mmol). The reaction mixture was cooled to 0° C. and N-methylmorpholine-N-oxide (4.89 g, 41.8 mmol) was added. This mixture was allowed to warm up slowly to room temperature over 2 hours. The reaction was quenched with aqueous sodium sulfite solution and diluted with EtOAc. The layers were separated and the aqueous layer was extracted with (2×100 mL) EtOAc. The organic portions were washed with brine, dried over MgSO$_4$ and concentrated under vacuum. Column chromatography on silica gel (70-100% ethyl acetate/hexanes) afforded intermediate 3 (5.99 g, 18.8 mmol, 90%). $^1$H NMR (400 MHz, CHLOROFORM-D) δ ppm 3.75-3.81 (m, 2H) 3.87 (d, J=2.52 Hz, 6H) 4.43-4.54 (m, 2H) 4.54-4.64 (m, 2H) 5.03 (dd, J=6.92, 4.91 Hz, 1H) 6.81-6.85 (m, 1H) 6.86-6.91 (m, 2H) 7.26-7.30 (m, 2H) 7.33-7.39 (m, 1H) 7.51 (d, J=7.55 Hz, 1H). Mass spec.: 319.36 (MH)$^+$.

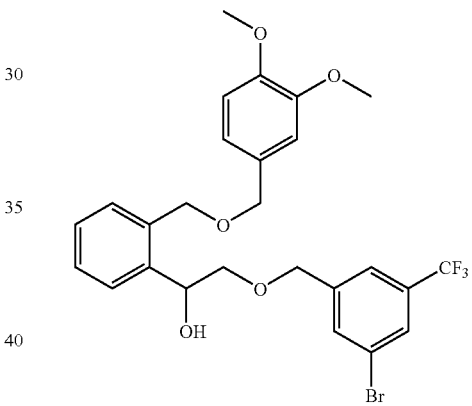

Intermediate 4

2-(3-bromo-5-(trifluoromethyl)benzyloxy)-1-(2-((3,4-dimethoxybenzyloxy)methyl)phenyl)ethanol. A stirred solution of 1-(2-((3,4-dimethoxybenzyloxy)methyl)phenyl)ethane-1,2-diol (2.17 g, 6.81 mmol) in dry toluene (150 mL), was treated with dibutyltinoxide (2.03 g, 8.17 mmol) then heated to reflux under a Dean-Stark trap for 1.5 hours to remove any excess water. The reaction mixture was cooled to 75° C. and tetrabutylammonium bromide (2.74 g, 8.52 mmol) was added, followed by the addition of 1-bromo-3-(bromomethyl)-5-(trifluoromethyl)benzene (2.6 g, 8.17 mmol). The resulting mixture was allowed to stir at 100° C. for 6 hours then cooled to room temperature and concentrated under vacuum. Column chromatography on silica gel (20-50% ethyl acetate/hexanes) afforded intermediate 4 (2.83 g, 5.09 mmol, 74%). $^1$H NMR (400 MHz, CHLOROFORM-D) δ ppm 3.82-3.88 (m, 6H) 4.40-4.64 (m, 8H) 5.20-5.26 (m, 1H) 6.77-6.82 (m, 1H) 6.84-6.88 (m, 2H) 7.27-7.32 (m, 2H) 7.34-7.39 (m, 1H) 7.46-7.49 (m, 1H) 7.54 (d, J=7.81 Hz, 1H) 7.65 (d, J=13.09 Hz, 2H). Mass spec.: 556.38 (MH)$^+$.

Intermediate 5

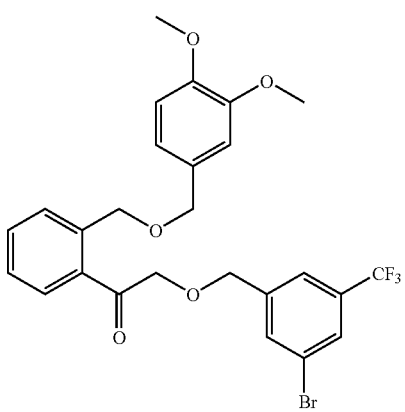

2-(3-bromo-5-(trifluoromethyl)benzyloxy)-1-(2-((3,4-dimethoxybenzyloxy)methyl)phenyl)ethanone. To a stirred solution of 2-(3-bromo-5-(trifluoromethyl)benzyloxy)-1-(2-((3,4-dimethoxybenzyloxy)methyl)phenyl)ethanol (2.83 g, 5.09 mmol) in $CH_2Cl_2$ (20 mL), was added Dess-Martin Periodinane (2.80 g, 6.62 mmol). The resulting mixture was stirred at room temperature for 4 hours then diluted with $CH_2Cl_2$, washed with aqueous $Na_2S_2O_3$, saturated $NaHCO_3$, and brine. The organics were dried over $MgSO_4$ and concentrated under vacuum. Column chromatography on silica gel (10-30% ethyl acetate/hexanes) afforded intermediate 5 (1.91 g, 3.45 mmol, 67%). $^1$H NMR (400 MHz, CHLOROFORM-D) δ ppm 3.86 (t, J=3.53 Hz, 6H) 4.50 (s, 2H) 4.54 (s, 2H) 4.63 (s, 2H) 4.79 (s, 2H) 6.79-6.82 (m, 1H) 6.85-6.91 (m, 2H) 7.31-7.39 (m, 1H) 7.45-7.55 (m, 3H) 7.60 (d, J=7.30 Hz, 1H) 7.64 (d, J=15.36 Hz, 2H). Mass spec.: 554.36 (MH)$^+$.

Intermediate 6

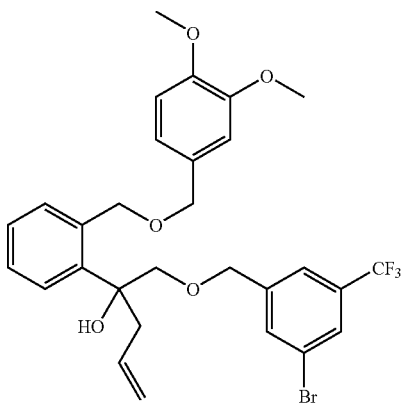

3-bromo-5-(trifluoromethyl)benzyloxy)-1-(2-((3,4-dimethoxybenzyloxy)methyl)phenyl)ethanone. To a well stirred solution of 2-(3-bromo-5-(trifluoromethyl)benzyloxy)-1-(2-((3,4-dimethoxybenzyloxy)methyl)phenyl)ethanone (1.91 g, 3.45 mmol) and allyl bromide (0.60 mL, 6.90 mmol) in a mixture of THF (10 mL) and $H_2O$ (10 mL), was added indium (0) (792 mg, 6.90 mmol). The resulting mixture was stirred at room temperature for 4 hours. The reaction was diluted with ether and treated with 1.0 N HCl. The layers were separated and the ether layer was washed with $H_2O$ and brine then dried over $MgSO_4$ and concentrated under vacuum to afford crude intermediate 6 (2.10 g, 3.52 mmol, >100%). $^1$H NMR (400 MHz, CHLOROFORM-D) δ ppm 2.57-2.67 (m, 1H) 2.67-2.77 (m, 1H) 3.65 (d, J=9.57 Hz, 1H) 3.71-3.81 (m, 1H) 3.81-3.89 (m, 6H) 4.42-4.52 (m, 4H) 4.73-4.88 (m, 2H) 4.92-5.09 (m, 2H) 5.55-5.76 (m, 1H) 6.76-6.89 (m, 3H) 7.19-7.36 (m, 5H) 7.46 (s, 1H) 7.61 (s, 1H). Mass spec.: 596.44 (MH)$^+$.

Intermediate 7

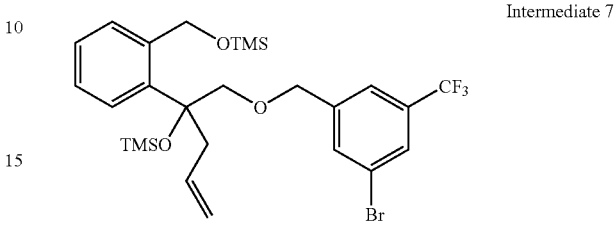

1-(3-bromo-5-(trifluoromethyl)benzyloxy)-2-(2-((trimethylsilyloxy)methyl)phenyl)pent-4-en-2-yloxy)trimethylsilane. To a stirred solution of 3-bromo-5-(trifluoromethyl)benzyloxy)-1-(2-((3,4-dimethoxybenzyloxy)methyl)phenyl)ethanone (2.10 g, 3.52 mmol) and triethylamine (1.76 mL, 12.6 mmol) in dry $CH_2Cl_2$ (20 mL), was added trimethylsilyl trifluoro-methanesulfonate (2.10 mL, 11.6 mmol). The mixture was allowed to stir at room temperature overnight. The reaction was dissolved in $CH_2Cl_2$, washed with saturated $NaHCO_3$ and brine, dried over $MgSO_4$ and concentrated under vacuum. Column chromatography on silica gel (0-10% ethyl acetate/hexanes) afforded intermediate 7 (1.41 g, 2.39 mmol, 68%). $^1$H NMR (400 MHz, CHLOROFORM-D) δ ppm 0.07-0.09 (m, 9H) 0.15-0.17 (m, 9H) 2.78 (d, J=6.80 Hz, 2H) 3.64-3.73 (m, 1H) 3.74-3.82 (m, 1H) 4.49 (s, 2H) 4.89-5.10 (m, 4H) 5.46-5.72 (m, 1H) 7.09-7.19 (m, 2H) 7.25-7.29 (m, 1H) 7.46 (s, 1H) 7.58 (s, 1H) 7.64-7.69 (m, 2H). Mass spec.: 590.63 (MH)$^+$.

Intermediate 8

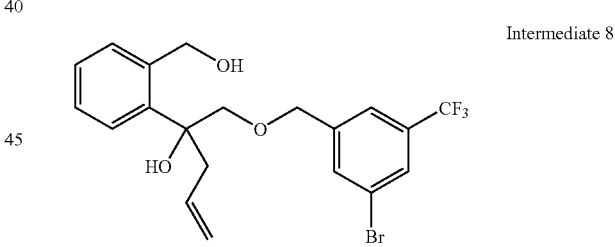

1-(3-bromo-5-(trifluoromethyl)benzyloxy)-2-(2-(hydroxymethyl)phenyl)pent-4-en-2-ol. To a stirred solution of 1-(3-bromo-5-(trifluoromethyl)benzyloxy)-2-(2-((trimethylsilyloxy)methyl)phenyl)pent-4-en-2-yloxy)trimethylsilane (1.41 g, 2.39 mmol) in THF (10 mL), was added 1.0 M solution of tetrabutylammonium fluoride in THF (4.78 mL, 4.78 mmol) and the mixture was allowed to stir at room temperature for 1 hour. The reaction mixture was diluted with EtOAc and washed with saturated $NaHCO_3$ and brine then dried over $MgSO_4$ and concentrated under vacuum to afford crude intermediate 8 (1.21 g, 2.69 mmol, >100%). $^1$H NMR (400 MHz, CHLOROFORM-D) δ ppm 2.76 (d, J=7.30 Hz, 2H) 3.65-3.78 (m, 2H) 4.58 (s, 2H) 4.67-4.77 (m, 1H) 4.78-4.88 (m, 1H) 4.99-5.14 (m, 2H) 5.55-5.71 (m, 1H) 7.09-7.15 (m, 1H) 7.25-7.29 (m, 2H) 7.30-7.34 (m, 1H) 7.42 (s, 1H) 7.56 (s, 1H) 7.67 (s, 1H). Mass spec.: 446.27 (MH$^+$)$^+$.

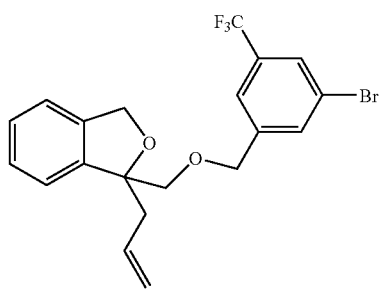

Intermediate 9

1-allyl-1-((3-bromo-5-(trifluoromethyl)benzyloxy)methyl)-1,3-dihydroisobenzofuran. To a stirred solution of 1-(3-bromo-5-(trifluoromethyl)benzyloxy)-2-(2-(hydroxymethyl)phenyl)pent-4-en-2-ol (1.2 g, 2.69 mmol) in dry $CH_2Cl_2$ (10 mL) and triethylamine (0.56 mL, 4.04 mmol) cooled to 0° C., was slowly added methanesulfonyl chloride (0.25 mL, 3.23 mmol). The reaction mixture was stirred at 0° C. for 1 hour then diluted with $CH_2Cl_2$, washed with saturated $NaHCO_3$ and brine, dried over $MgSO_4$ and concentrated under vacuum. Column chromatography on silica gel (0-10% ethyl acetate/hexanes) afforded intermediate 9 (801 mg, 1.87 mmol, 70%). $^1$H NMR (400 MHz, CHLOROFORM-D) δ ppm 2.51-2.76 (m, 2H) 3.64 (s, 2H) 4.45-4.59 (m, 2H) 4.92-5.14 (m, 4H) 5.59-5.77 (m, 1H) 7.13-7.18 (m, 1H) 7.19-7.22 (m, 1H) 7.26-7.31 (m, 2H) 7.39 (s, 1H) 7.53 (s, 1H) 7.63 (s, 1H). Mass spec.: 428.25 $(MH)^+$.

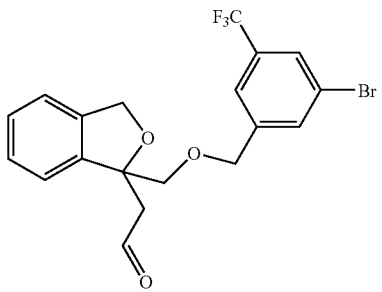

Intermediate 10

2-(1-((3-bromo-5-(trifluoromethyl)benzyloxy)methyl)-1,3-dihydroisobenzofuran-1-yl)acetaldehyde. 1-allyl-1-((3-bromo-5-(trifluoromethyl)benzyloxy)methyl)-1,3-dihydroisobenzofuran (801 mg, 1.87 mmol) was dissolved in a mixture of 1,4-dioxane (8 mL) and $H_2O$ (8 mL). Sodium periodate (1.19 g, 5.60 mmol) was added at room temperature followed after 5 minutes by addition of Osmium tetroxide 2.5 wt. % solution in 2-methyl-2-propanol (1.14 mL, 0.112 mmol). Stirring at room temperature was continued for 1.5 hours. The reaction mixture was quenched with saturated $Na_2SO_3$ and diluted with EtOAc. The layers were separated and the aqueous layer was extracted with EtOAc. The combined EtOAc layers were washed with brine, dried over $MgSO_4$ and concentrated under vacuum. Column chromatography on silica gel (2-20% ethyl acetate/hexanes) afforded intermediate 10 (485 mg, 1.12 mmol, 60%). $^1$H NMR (400 MHz, CHLOROFORM-D) δ ppm 2.81-2.92 (m, 1H) 2.95-3.05 (m, 1H) 3.59-3.72 (m, 2H) 4.57 (s, 2H) 5.17 (s, 2H) 7.20 (d, J=6.80 Hz, 2H) 7.27-7.37 (m, 2H) 7.41 (s, 1H) 7.56 (s, 1H) 7.65 (s, 1H) 9.65 (t, J=2.77 Hz, 1H).). Mass spec.: 430.23 $(MH)^+$.

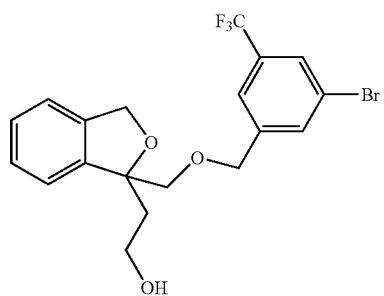

Intermediate 11

2-(1-((3-bromo-5-(trifluoromethyl)benzyloxy)methyl)-1,3-dihydroisobenzofuran-1-yl)ethanol. To a stirred solution of 2-(1-((3-bromo-5-(trifluoromethyl)benzyloxy)methyl)-1,3-dihydroisobenzofuran-1-yl)acetaldehyde (471 mg, 1.09 mmol) in EtOH (8 mL) cooled to 0° C., was added sodium borohydride (41 mg, 1.09 mmol). The ice bath was removed and the reaction mixture continued to stir at room temperature for 1 hour then was re-cooled to 0° C. and quenched slowly with saturated aqueous $NH_4Cl$ solution. The crude mixture was concentrated under vacuum and the resulting residue was suspended in $H_2O$ and extracted with EtOAc. The organic layer was washed with brine, dried over $MgSO_4$ and concentrated under vacuum. Column chromatography on silica gel (20-50% ethyl acetate/hexanes) afforded intermediate 11 (440 mg, 1.02 mmol, 93%). $^1$H NMR (400 MHz, CHLOROFORM-D) δ ppm 2.04-2.14 (m, 1H) 2.19-2.41 (m, 1H) 2.63 (dd, J=6.55, 4.53 Hz, 1H) 3.53-3.73 (m, 3H) 4.42-4.62 (m, 2H) 5.08-5.22 (m, 2H) 7.07-7.18 (m, 1H) 7.21-7.26 (m, 1H) 7.26-7.34 (m, 2H) 7.35 (s, 1H) 7.49 (s, 1H) 7.63 (s, 1H). Mass spec.: 432.24 $(MH)^+$.

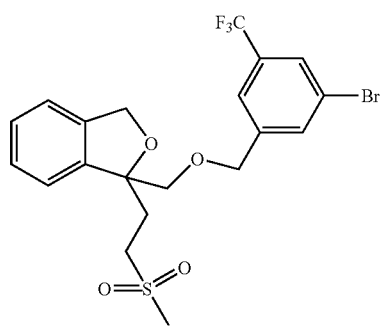

Intermediate 12

1-((3-bromo-5-(trifluoromethyl)benzyloxy)methyl)-1-(2-(methylsulfonyl)ethyl)-1,3-dihydroisobenzofuran. To a stirred solution of 2-(1-((3-bromo-5-(trifluoromethyl)benzyloxy)methyl)-1,3-dihydroisobenzofuran-1-yl)ethanol (440 mg, 1.02 mmol) in dry $CH_2Cl_2$ (5 mL) and triethylamine (0.25 mL, 1.83 mmol) cooled to 0° C., was added methanesulfonyl chloride (0.12 mL, 1.53 mmol). The reaction mixture was stirred at 0° C. for 1 hour then diluted with $CH_2Cl_2$ and washed with saturated $NaHCO_3$ and brine, dried over $MgSO_4$, filtered and concentrated under vacuum to afford crude intermediate 12 (420 mg, 0.851 mmol). $^1$H NMR (400 MHz, CHLOROFORM-D) δ ppm 2.26-2.40 (m, 1H) 2.41-

2.53 (m, 1H) 2.74-2.79 (m, 3H) 3.59 (s, 2H) 4.04-4.17 (m, 1H) 4.22-4.34 (m, 1H) 4.54 (s, 2H) 5.12 (s, 2H) 7.16-7.24 (m, 2H) 7.28-7.34 (m, 2H) 7.38 (s, 1H) 7.52 (s, 1H) 7.64 (s, 1H). Mass spec.: 494.33 (MH)+.

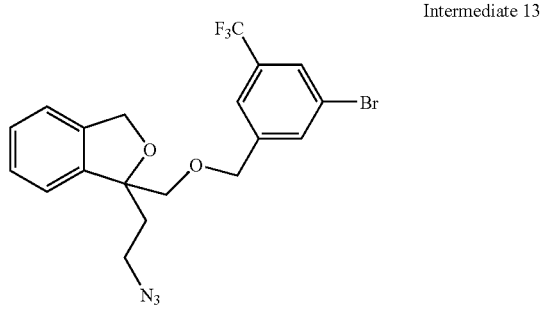

Intermediate 13

1-(2-azidoethyl)-1-((3-bromo-5-(trifluoromethyl)benzyloxy)methyl)-1,3-dihydroisobenzofuran. To a stirred solution of crude 1-((3-bromo-5-(trifluoromethyl)benzyloxy)methyl)-1-(2-(methylsulfonyl)ethyl)-1,3-dihydroisobenzofuran (420 mg, 0.851 mmol) in DMSO (5 mL), was added sodium azide (431 mg, 6.63 mmol). The reaction mixture was heated at 60° C. for 3 hours then cooled and diluted with H₂O and ether. The layers were separated and the ether layer was washed with brine, dried over MgSO₄ and concentrated under vacuum. Column chromatography on silica gel (2-20% ethyl acetate/hexanes) afforded intermediate 13 (397 mg, 0.870 mmol, 85%). ¹H NMR (400 MHz, CHLOROFORM-D) δ ppm 2.05-2.19 (m, 1H) 2.23-2.37 (m, 1H) 2.94-3.13 (m, 1H) 3.25-3.41 (m, 1H) 3.59 (s, 2H) 4.53 (s, 2H) 5.11 (s, 2H) 7.13-7.19 (m, 1H) 7.20-7.24 (m, 1H) 7.29-7.34 (m, 2H) 7.38 (s, 1H) 7.52 (s, 1H) 7.63 (s, 1H). Mass spec.: 457.26 (MH)+.

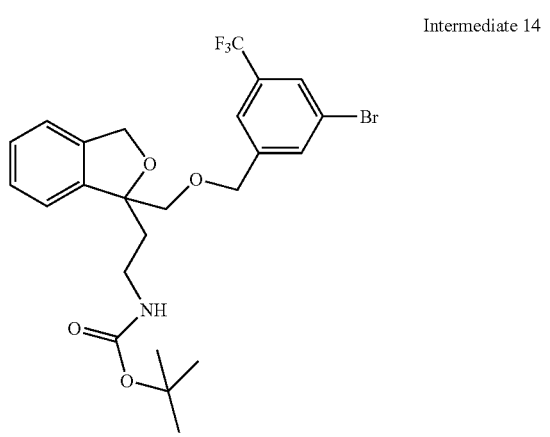

Intermediate 14 tert-butyl 2-(1-((3-bromo-5-(trifluoromethyl)benzyloxy)methyl-1,3-dihydroisobenzofuran-1-yl)ethylcarbamate. To a solution of 2-(1-((3-bromo-5-(trifluoromethyl)benzyloxy)methyl)-1,3-dihydroisobenzofuran-1-yl)ethanamine (300 mg, 0.697 mmol) in THF (6 mL), was added di-tert-butyl dicarbonate (152 mg, 0.697 mmol), triethylamine (0.11 mL, 0.836 mmol), and N,N-dimethyl-4-amino pyridine (8.5 mg, 0.0697 mmol). The mixture was stirred at room temperature for 1.5 hours then partitioned between EtOAc and water. The layers were separated and the organic layer was washed with brine, dried over MgSO₄ and concentrated under vacuum. Column chromatography on silica gel (10-30% ethyl acetate/hexanes) afforded intermediate 14 (364 mg, 0.686 mmol, 98%). ¹H NMR (400 MHz, CHLOROFORM-D) δ ppm 1.37-1.44 (m, 9H) 2.05-2.21 (m, 2H) 2.85-3.19 (m, 2H) 3.59 (s, 2H) 4.38-4.59 (m, 2H) 5.12 (s, 2H) 7.12-7.17 (m, 1H) 7.19-7.23 (m, 1H) 7.26-7.33 (m, 2H) 7.36 (s, 1H) 7.50 (s, 1H) 7.62 (s, 1H). Mass spec.: 531.37 (MH)+.

EXAMPLE 1

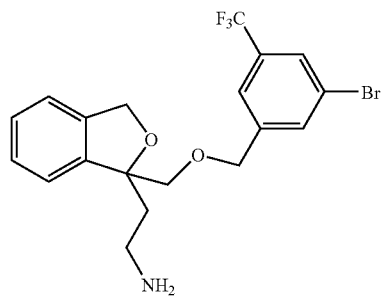

2-(1-((3-bromo-5-(trifluoromethyl)benzyloxy)methyl)-1,3-dihydroisobenzofuran-1-yl)ethanamine. To a stirred solution of 1-(2-azidoethyl)-1-((3-bromo-5-(trifluoromethyl)benzyloxy)methyl)-1,3-dihydroisobenzofuran (397 mg, 0.870 mmol) in THF (10 mL), was added triphenylphosphine (273 mg, 1.04 mmol). The reaction was allowed to stir at room temperature for 15 minutes. Water (2.5 mL) was added and the reaction mixture was heated at 55° C. for 3 hours then cooled, further diluted with H₂O and extracted with (2×25 mL) EtOAc. The combined EtOAc layers were dried over MgSO₄, filtered and concentrated under vacuum. Column chromatography on silica gel (0-12% MeOH/CH₂Cl₂) afforded pure compound in example 1 (317 mg, 0.736 mmol, 84%). ¹H NMR (500 MHz, MeOD) δ ppm 1.96-2.23 (m, 2H) 2.42-2.52 (m, 1H) 2.62-2.74 (m, 1H) 3.61-3.74 (m, 2 H) 4.46-4.65 (m, 2H) 5.05-5.18 (m, 2H) 7.19-7.38 (m, 4H) 7.49 (s, 1H) 7.63 (s, 1H) 7.71 (s, 1H). Mass spec.: 431.26 (MH)+.

EXAMPLE 2

3'-(((1-(2-aminoethyl)-1,3-dihydroisobenzofuran-1-yl)methoxy)methyl)-5'-(trifluoromethyl)biphenyl-4-carbonitrile. To a stirred solution of tert-butyl 2-(1-((3-bromo-5-(trifluoromethyl)benzyloxy)methyl-1,3-dihydroisobenzofuran-1-yl)ethylcarbamate (30 mg, 0.056 mmol) in THF (2 mL), was added 4-cyanophenyl boronic acid (35 mg, 0.237 mmol) and tetrakis(triphenylphosphine) palladium(0) (6.5 mg, 0.0056 mmol) in a sealed microwave tube. The mixture was flushed with N₂, followed by the addition of 0.25 mL of 1N KOH aqueous solution to the reaction mixture. The mixture was heated in the microwave reactor at 120° C. for 1 hour the cooled, diluted with EtOAc and washed with H₂O and brine. The organic portion was dried over MgSO₄, filtered and concentrated under vacuum. Column chromatography on silica gel (15-35% ethyl acetate/hexanes) afforded BOC-protected intermediate of example 2 (28 mg, 0.050 mmol, 90%). This intermediate was then treated with a trifluoroacetic acid/methylene chloride mixture (1:2, 3 mL) for 1 hour. The solvent was removed in vacuo and the resulting crude mixture passed through a strong cation exchange column. After washing the column with several volumes of methanol, the product was eluted by washing the column with 2 M ammonia in methanol to afford pure compound in example 2 (12 mg, 0.026 mmol, 55%). ¹H NMR (400 MHz, MeOD) δ ppm 1.97-2.20 (m, 2H) 2.34-2.52 (m, 1H) 2.57-2.74 (m, 1H) 3.69 (s, 2H) 4.52-4.72 (m, 2H) 4.97-5.15 (m, 2H) 7.20-7.32 (m, 4H) 7.54 (s, 1H) 7.70 (s, 1H) 7.74-7.79 (m, 2H) 7.79-7.86 (m, 3H). Mass spec.: 453.47 (MH)⁺.

Table 2 describes compounds that were prepared by the method of Example 2. Retention time ($t_R$) is in min.

TABLE 2

| Example | Structure | MS (MH)⁺ | ¹H NMR |
|---|---|---|---|
| 3 | 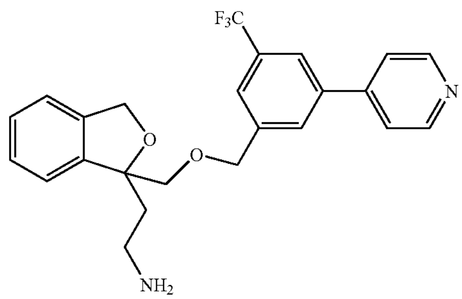 | 429.45 | ¹H NMR (400 MHz, DMSO-D6) δ ppm 1.81-2.03 (m, 2 H) 2.18-2.41 (m, 1 H) 2.53 (d,J = 3.78 Hz, 1 H) 3.57-3.73 (m, 2 H) 4.64 (d, J = 4.78 Hz, 2 H) 4.97-5.05 (m, 2 H) 7.27 (s, 4 H) 7.59 (s, 1 H) 7.72 (dd, J = 4.53, 1.51 Hz, 2 H) 7.85 (s, 1 H) 7.99 (s, 1 H) 8.62-8.72 (m, 2 H) |
| 4 | 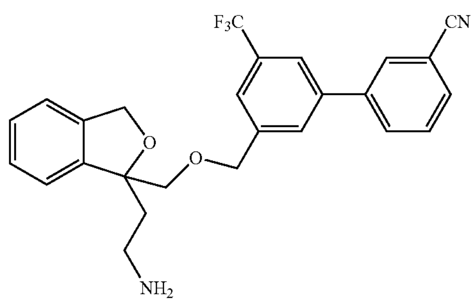 | 453.47 | ¹H NMR (400 MHz, MeOD) δ ppm 1.91-2.20 (m, 2 H) 2.31-2.48 (m, 1 H) 2.51-2.67 (m, 1 H) 3.54-3.72 (m, 2 H) 4.46 - 4.70 (m, 2 H) 4.95-5.14 (m, 2 H) 7.14-7.29 (m, 4 H) 7.47 (s, 1 H) 7.55-7.63 (m, 2 H) 7.66-7.75 (m, 2 H) 7.79-7.91 (m, 2 H) |
| 5 | 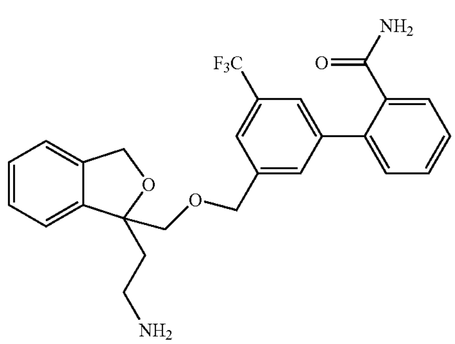 | 471.50 | ¹H NMR (400 MHz, MeOD) δ ppm 1.92-2.21 (m, 2 H) 2.34-2.47 (m, 1 H) 2.54-2.67 (m, 1 H) 3.49-3.68 (m, 2 H) 4.53 (s, 2 H) 4.91-5.13 (m, 2 H) 7.12-7.25 (m, 4 H) 7.30 (d, J = 7.81 Hz, 1 H) 7.34-7.43 (m, 2 H) 7.44-7.52 (m, 3 H) 7.54 (s, 1 H) |
| 6 | 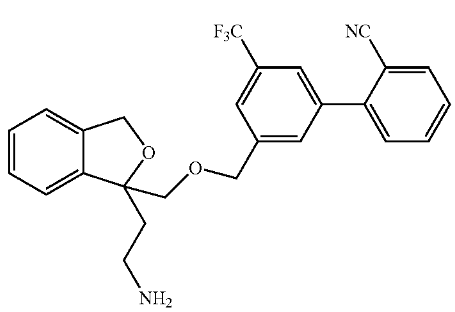 | 453.47 | 1 H NMR (400 MHz, MeOD) δ ppm 1.97-2.22 (m, 2 H) 2.45 (s, 1 H) 2.56-2.74 (m, 1 H) 3.56-3.72 (m, 2 H) 4.44-4.67 (m, 2 H) 4.93-5.14 (m, 2 H) 7.10-7.23 (m, 4 H) 7.46-7.57 (m, 4 H) 7.64 (s, 1 H) 7.71 (t, J = 7.68 Hz, 1 H) 7.80 (d, J = 7.55 Hz, 1 H) |

TABLE 2-continued
| Example | Structure | MS (MH)+ | ¹H NMR |
|---|---|---|---|
| 7 | 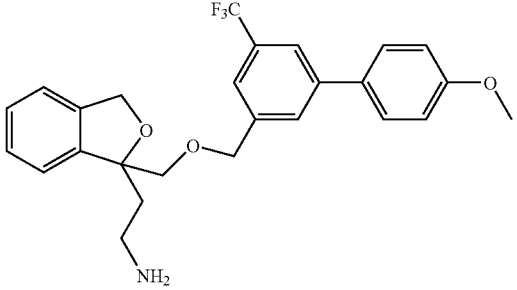 | 458.48 | ¹H NMR (400 MHz, MeOD) δ ppm 1.96-2.23 (m, 2 H) 2.34-2.55 (m, 1 H) 2.58-2.74 (m, 1 H) 3.66 (s, 2 H) 3.82 (s, 3 H) 4.58 (s, 2 H) 4.99-5.15 (m, 2 H) 6.95-7.05 (m, 2 H) 7.18-7.33 (m, 4 H) 7.38 (s, 1 H) 7.49 (d, J = 8.31 Hz, 2 H) 7.59 (s, 1 H) 7.67 (s, 1 H) |
| 8 | 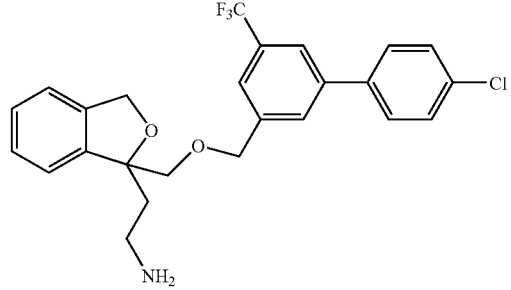 | 462.90 | ¹H NMR (400 MHz, MeOD) δ ppm 1.91-2.18 (m, 2 H) 2.33-2.49 (m, 1 H) 2.55-2.70 (m, 1 H) 3.55-3.71 (m, 2 H) 4.45-4.65 (m, 2 H) 4.92-5.14 (m, 2 H) 7.17-7.28 (m, 4 H) 7.39-7.45 (m, 3 H) 7.48-7.54 (m, 2 H) 7.59 (s, 1 H) 7.68 (s, 1 H) |
| 9 | 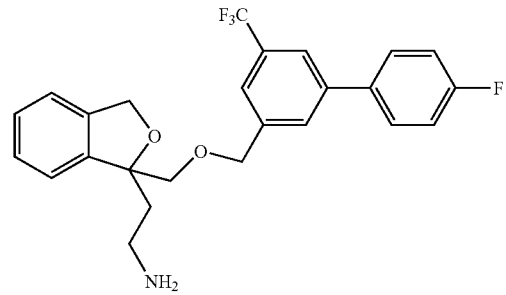 | 446.45 | ¹H NMR (400 MHz, MeOD) δ ppm 1.89-2.19 (m, 2 H) 2.29-2.48 (m, 1 H) 2.51-2.69 (m, 1 H) 3.55-3.73 (m, 2 H) 4.45-4.67 (m, 2 H) 4.91-5.15 (m, 2 H) 7.08-7.28 (m, 6 H) 7.41 (s, 1 H) 7.50-7.56 (m, 2 H) 7.57 (s, 1 H) 7.66 (s, 1 H) |
| 10 | 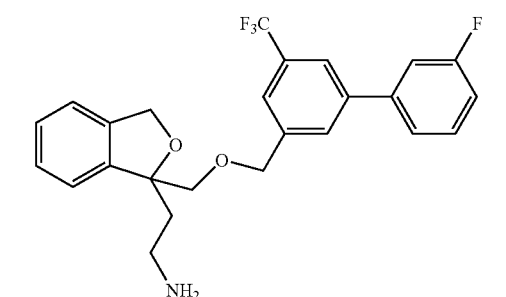 | 446.45 | ¹H NMR (400 MHz, MeOD) δ ppm 1.95-2.20 (m, 2 H) 2.40-2.50 (m, 1 H) 2.58-2.70 (m, 1 H) 3.63-3.71 (m, 2 H) 4.52-4.68 (m, 2 H) 4.97-5.18 (m, 2 H) 7.07-7.16 (m, 1 H) 7.20-7.33 (m, 5 H) 7.38 (d, J = 8.06 Hz, 1 H) 7.42-7.50 (m, 2 H) 7.63 (s, 1 H) 7.73 (s, 1 H) |
| 11 | 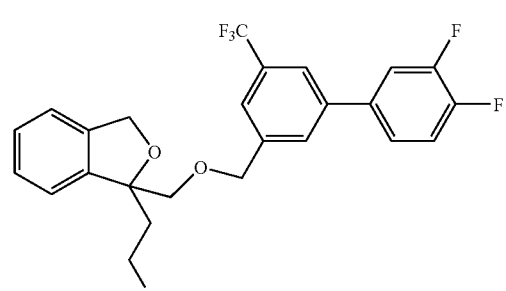 | 464.44 | ¹H NMR (400 MHz, MeOD) δ ppm 1.90-2.16 (m, 2 H) 2.33-2.50 (m, 1 H) 2.54-2.69 (m, 1 H) 3.59-3.72 (m, 2 H) 4.48-4.64 (m, 2 H) 4.96-5.17 (m, 2 H) 7.17-7.28 (m, 4 H) 7.29-7.38 (m, 2 H) 7.39-7.50 (m, 2 H) 7.57 (s, 1 H) 7.68 (s, 1 H) |

TABLE 2-continued

| Example | Structure | MS (MH)+ | 1H NMR |
|---|---|---|---|
| 12 | 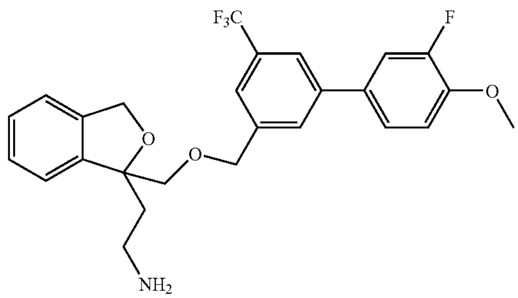 | 476.48 | 1H NMR (400 MHz, MeOD) δ ppm 1.93-2.19 (m, 2 H) 2.33-2.50 (m, 1 H) 2.56-2.71 (m, 1 H) 3.64 (s, 2 H) 3.87 (s, 3 H) 4.44-4.66 (m, 2 H) 4.92-5.17 (m, 2 H) 7.14 (t, J = 8.81 Hz, 1 H) 7.18-7.27 (m, 4 H) 7.27-7.34 (m, 2 H) 7.38 (s, 1 H) 7.55 (s, 1 H) 7.64 (s, 1 H) |
| 13 | 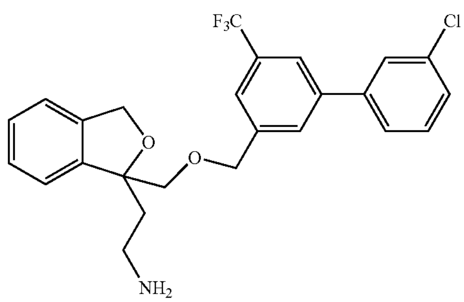 | 462.90 | 1H NMR (400 MHz, MeOD) δ ppm 1.89-2.21 (m, 2 H) 2.29-2.50 (m, 1 H) 2.50-2.73 (m, 1 H) 3.57-3.73 (m, 2 H) 4.46-4.68 (m, 2 H) 4.95-5.22 (m, 2 H) 7.16-7.29 (m, 4 H) 7.32-7.49 (m, 4 H) 7.54 (d, J = 1.51 Hz, 1 H) 7.58 (s, 1 H) 7.68 (s, 1 H) |
| 14 | 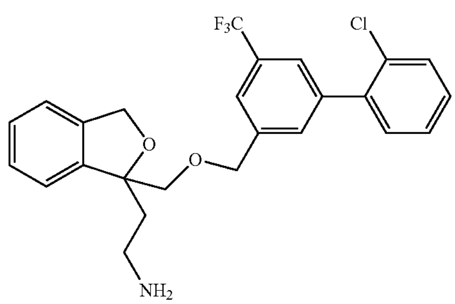 | 462.90 | 1H NMR (400 MHz, MeOD) δ ppm 1.88-2.21 (m, 2 H) 2.33-2.51 (m, 1 H) 2.50-2.70 (m, 1 H) 3.55-3.74 (m, 2 H) 4.47-4.65 (m, 2 H) 4.92-5.14 (m, 2 H) 7.14-7.21 (m, 4 H) 7.24-7.30 (m, 1 H) 7.32-7.37 (m, 2 H) 7.39 (s, 1 H) 7.43-7.52 (m, 3 H) |
| 15 | 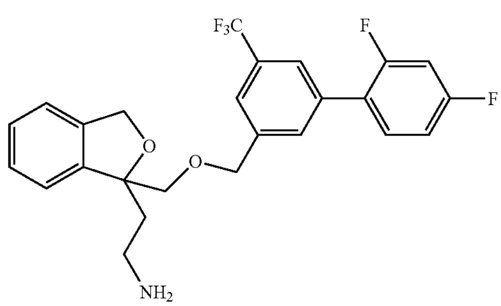 | 464.44 | 1H NMR (400 MHz, MeOD) δ ppm 1.87-2.17 (m, 2 H) 2.30-2.47 (m, 1 H) 2.53-2.71 (m, 1 H) 3.63 (s, 2 H) 4.46-4.64 (m, 2 H) 4.94-5.13 (m, 2 H) 6.98-7.09 (m, 2 H) 7.15-7.26 (m, 4 H) 7.38-7.44 (m, 1 H) 7.45 (s, 1 H) 7.49 (s, 1 H) 7.60 (s, 1 H) |

EXAMPLE 16

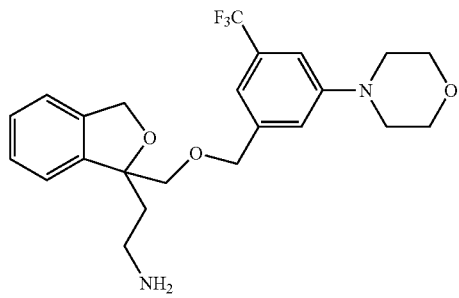

2-(1-((3-morpholino-5-(trifluoromethyl)benzyloxy)methyl)-1,3-dihydroisobenzofuran-1-yl)ethanamine. To a solution of tert-butyl 2-(1-((3-bromo-5-(trifluoromethyl)benzyloxy)methyl-1,3-dihydroisobenzofuran-1-yl)ethylcarbamate (31 mg, 0.058 mmol), was added sodium tert-butoxide (8 mg, 0.087 mmol), morpholine (0.006 mL, 0.070 mmol), and tris(dibenzylideneacetone)dipalladium (0) (2 mg, 0.0014 mmol). The ligand (2,8,9-triisobutyl(-2,5,8,9-tetraaza-1-phosphabicyclo[3.3.3]undecane) (0.002 mL, 0.0058 mmol) was then added. The reaction mixture was heated to reflux for 4 hours, cooled, concentrated under vacuum and the crude residue was dissolved in EtOAc and washed with H$_2$O and brine. The organic portions were dried over MgSO$_4$, filtered and concentrated under vacuum. Column chromatography on silica gel (25-40% ethyl acetate/hexanes) afforded BOC-protected intermediate of example 16 (18 mg, 0.033 mmol, 58%). This intermediate was then treated with a trifluoroacetic acid/methylene chloride mixture (1:2, 3 mL) for 1 hour. The solvent was removed in vacuo and the resulting crude mixture passed through a strong cation exchange column. After washing the column with several volumes of methanol, the product was eluted by washing the column with 2 M ammonia in methanol to afford pure compound in example 16 (5 mg, 0.011 mmol, 35%). $^1$H NMR (400 MHz, DMSO-D6) δ ppm 1.93 (s, 2H) 2.28 (s, 2H) 3.12 (d, J=4.53 Hz, 4H) 3.48-3.64 (m, 2H) 3.67-3.81 (m, 4H) 4.49 (s, 2H) 5.00 (s, 2H) 6.90 (s, 1H) 6.97 (s, 1H) 7.05 (s, 1H) 7.24-7.32 (m, 4H). Mass spec.: 437.47 (MH$^+$)$^+$.

EXAMPLE 17

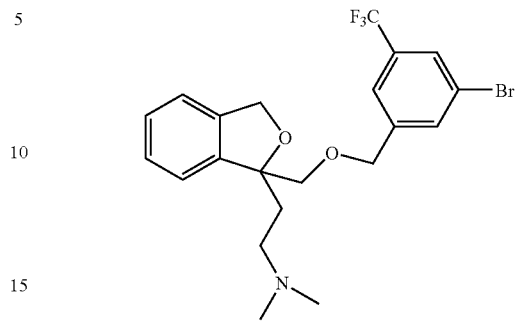

2-(1-((3-bromo-5-(trifluoromethyl)benzyloxy)methyl)-1,3-dihydroisobenzofuran-1-yl)-N,N-dimethylethanamine. To a stirred solution of 2-(1-((3-bromo-5-(trifluoromethyl)benzyloxy)methyl)-1,3-dihydroisobenzofuran-1-yl)acetaldehyde (25 mg, 0.058 mmol) in MeCN (1 mL) cooled to 0° C., was added 2.0 M solution of dimethylamine in THF (0.043 mL, 0.087 mmol). After 5 minutes, sodium borohydride (11 mg, 0.174 mmol) was added, followed by a drop of acetic acid. The mixture was stirred at 0° C. for 1 hour. The reaction mixture was diluted with ether and H$_2$O and the layers were separated. The aqueous layer was made lightly basic and extracted with ether. The combined ether layers were washed with brine, dried over MgSO$_4$, filtered and concentrated under vacuum. Column chromatography on silica gel (0-8% MeOH/CH$_2$Cl$_2$) afforded intermediate 16 (18 mg, 0.039 mmol, 69%). $^1$H NMR (500 MHz, CHLOROFORM-D) δ ppm 1.64 (s, 2H) 2.42 (s, 1H) 2.51-2.63 (m, 6H) 2.83 (s, 1H) 3.54-3.67 (m, 2H) 4.48-4.62 (m, 2H) 5.01-5.18 (m, 2H) 7.18-7.27 (m, 2H) 7.29-7.37 (m, 2H) 7.39 (s, 1H) 7.53 (s, 1H) 7.64 (s, 1H). Mass spec.: 459.31 (MH)$^+$.

Table 3 describes compounds that were prepared from 2-(1-((3-bromo-5-(trifluoromethyl)benzyloxy)methyl)-1,3-dihydroisobenzofuran-1-yl)-N,N-dimethylethanamine following the experimental conditions described in Example 2 for Suzuki couplings. Retention time (t$_R$) is in min.

TABLE 3

| Example | Structure | MS (MH)$^+$ | $^1$H NMR |
|---|---|---|---|
| 18 | ![structure] | 481.52 | $^1$H NMR (400 MHz, MeOD) δ ppm 1.96-2.14 (m, 3 H) 2.17 (s, 6 H) 2.43 (s, 1 H) 3.63 (s, 2 H) 4.58 (d, J = 4.53 Hz, 2 H) 5.02 (d, J = 5.04 Hz, 2 H) 7.14-7.27 (m, 4 H) 7.50 (s, 1 H) 7.66 (s, 1 H) 7.69-7.73 (m, 2 H) 7.74-7.79 (m, 3 H) |

TABLE 3-continued

| Example | Structure | MS (MH)+ | ¹H NMR |
|---------|-----------|----------|--------|
| 19 | 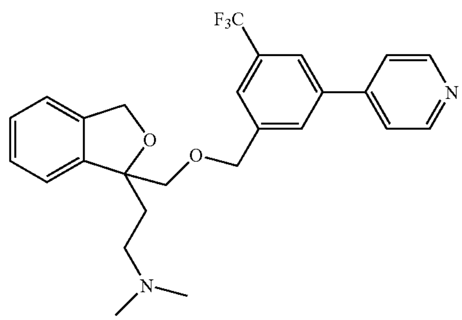 | 457.50 | ¹H NMR (400 MHz, MeOD) δ ppm 1.95-2.13 (m, 3 H) 2.16 (s, 6 H) 2.30-2.52 (m, 1 H) 3.64 (s, 2 H) 4.49-4.67 (m, 2 H) 4.96-5.12 (m, 2 H) 7.15-7.27 (m, 4 H) 7.54 (s, 1 H) 7.61 (dd, J = 4.66, 1.64 Hz, 2 H) 7.73 (s, 1 H) 7.83 (s, 1 H) 8.55 (dd, J = 4.66, 1.64 Hz, 2 H) |

EXAMPLE 20

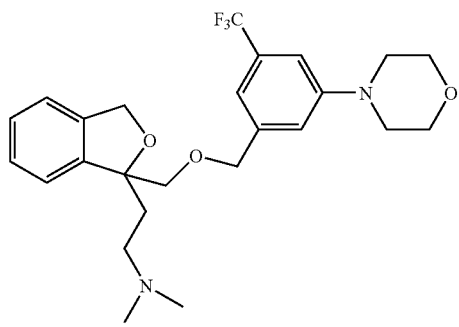

N,N-dimethyl-2-(1-((3-morpholino-5-(trifluoromethyl)benzyloxy)methyl)-1,3-dihydroisobenzofuran-1-yl)ethanamine. This compound was prepared according to the experimental condition of Example 16 from 2-(1-((3-bromo-5-(trifluoromethyl)benzyloxy)methyl)-1,3-dihydroisobenzofuran-1-yl)-N,N-dimethylethanamine to afford 5.3 mg (0.011 mmol, 29%). ¹H NMR (400 MHz, MeOD) δ ppm 2.08 (s, 3H) 2.25 (s, 6H) 2.50 (s, 1H) 3.02-3.17 (m, 2H) 3.21-3.37 (m, 5H) 3.55-3.71 (m, 2H) 3.74-3.86 (m, 1H) 4.55 (d, J=7.30 Hz, 2H) 5.07 (s, 2H) 6.93 (s, 1H) 7.20-7.34 (m, 4H) 7.47 (s, 1H) 7.61 (s, 1H). Mass spec.: 465.52 (MH)+.

Intermediate 15

4-bromo-3-(bromomethyl)benzonitrile. To a stirred solution of 4-bromo-3-methyl benzonitrile (5 g, 25.5 mmol) in CCl₄ (200 mL), was added N-bromosuccinimide (4.99 g, 28.05 mmol) and 2,2-Azobisisobutyronitrile (335 mg, 2.04 mmol). The mixture was heated to reflux overnight then cooled, diluted with CH₂Cl₂ and quenched with 10% NaHSO₃. The layers were separated and the CH₂Cl₂ layer was washed with saturated NaHCO₃ and brine, dried over MgSO₄, filtered and concentrated under vacuum. Column chromatography on silica gel (5-10% ethyl acetate/hexanes) afforded 4.31 g (3.65 mmol, 61%) of a mixture of mono- and di-bromo intermediates. ¹H NMR (400 MHz, CHLOROFORM-D) δ ppm 4.55 (s, 2H) 7.42 (dd, J=8.31, 2.01 Hz, 1H) 7.67-7.78 (m, 2H). Mass spec.: 275.94 (MH)+.

Table 4 describes compounds that were prepared from 4-bromo-3-(bromomethyl)benzonitrile by following the experimental conditions described for the intermediates (1-14) and examples (1, 2 and 17). Retention time (t$_R$) is in min.

TABLE 4

| Example | Structure | MS (MH)+ | ¹H NMR |
|---------|-----------|----------|--------|
| 21 | 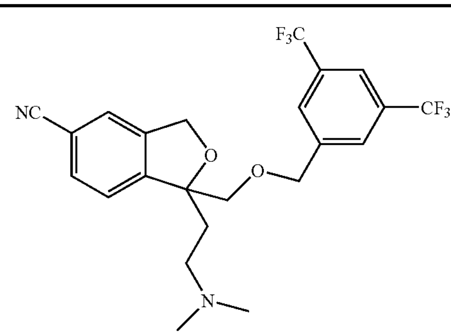 | 473.42 | ¹H NMR (400 MHz, CHLOROFORM-D) δ ppm 2.11-2.32 (m, 3 H) 2.37 (s, 6 H) 2.60 (s, 1 H) 3.64 (s, 2 H) 4.60 (d, J = 6.80 Hz, 2 H) 5.11 (s, 2 H) 7.35 (d, J = 7.05 Hz, 1 H) 7.51 (s, 1 H) 7.60 (s, 3 H) 7.76 (s, 1 H) |

TABLE 4-continued

| Example | Structure | MS (MH)+ | 1H NMR |
|---|---|---|---|
| 22 | 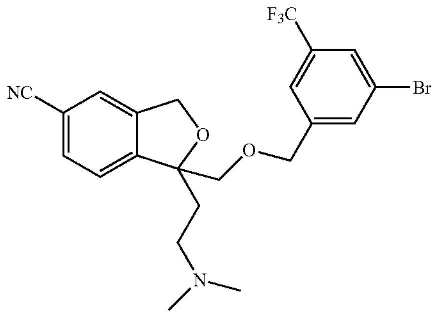 | 484.32 | 1H NMR (400 MHz, MeOD) δ ppm 2.04-2.17 (m, 3 H) 2.23 (d, J = 1.76 Hz, 6 H) 2.48 (d, J = 4.53 Hz, 1 H) 3.64-3.77 (m, 2 H) 4.55 (q, J = 13.09 Hz, 2 H) 5.11 (s, 2 H) 7.42 (s, 1 H) 7.46 (d, J = 7.81 Hz, 1 H) 7.54 (s, 1 H) 7.64-7.68 (m, 2 H) 7.70 (s, 1 H) |
| 23 | 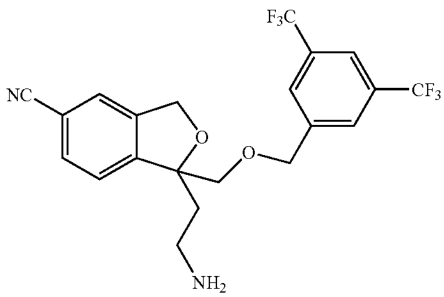 | 445.37 | 1H NMR (400 MHz, MeOD) δ ppm 2.05-2.31 (m, 2 H) 2.49-2.63 (m, 1 H) 2.69-2.82 (m, 1 H) 3.59-3.82 (m, 2 H) 4.47-4.71 (m, 2 H) 5.13 (s, 2 H) 7.45 (d, J = 7.81 Hz, 1 H) 7.64-7.73 (m, 4 H) 7.82 (s, 1 H) |
| 24 | 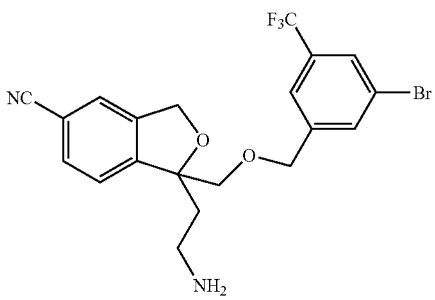 | 456.27 | 1H NMR (400 MHz, CHLOROFORM-D) δ ppm 1.96-2.24 (m, 2 H) 2.60 (d, J = 13.60 Hz, 1 H) 2.74 (d, J = 6.55 Hz, 3 H) 3.49-3.69 (m, 2 H) 4.34-4.60 (m, 2 H) 5.02-5.21 (m, 2 H) 7.27 (d, J = 7.81 Hz, 1 H) 7.31 (s, 1 H) 7.43 (s, 1 H) 7.51 (s, 1 H) 7.55-7.66 (m, 2 H) |
| 25 | 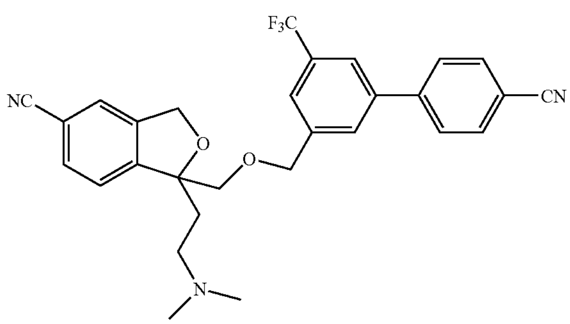 | 506.53 | 1H NMR (400 MHz, MeOD) δ ppm 1.96-2.14 (m, 3 H) 2.17 (s, 6 H) 2.36-2.49 (m, 1 H) 3.67-3.77 (m, 2 H) 4.50-4.71 (m, 2 H) 5.01-5.23 (m, 2 H) 7.41-7.52 (m, 2 H) 7.58-7.68 (m, 3 H) 7.73-7.78 (m, 2 H) 7.83 (t, J = 7.81 Hz, 3 H) |
| 26 | 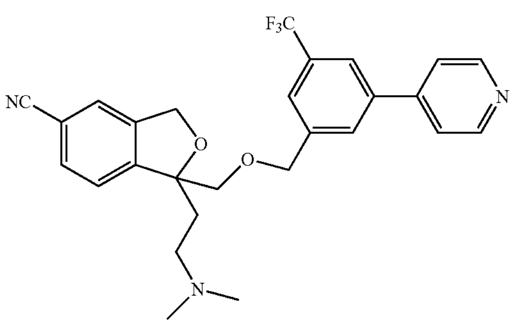 | 482.51 | 1H NMR (400 MHz, MeOD) δ ppm 1.93-2.10 (m, 3 H) 2.12 (s, 6 H) 2.38 (d, J = 5.04 Hz, 1 H) 3.55-3.77 (m, 2 H) 4.43-4.68 (m, 2 H) 5.06 (d, J = 3.27 Hz, 2 H) 7.41 (d, J = 8.31 Hz, 1 H) 7.50 (s, 1 H) 7.54-7.60 (m, 2 H) 7.61-7.65 (m, 2 H) 7.70 (s, 1 H) 7.85 (s, 1 H) 8.55-8.62 (m, 2 H) |

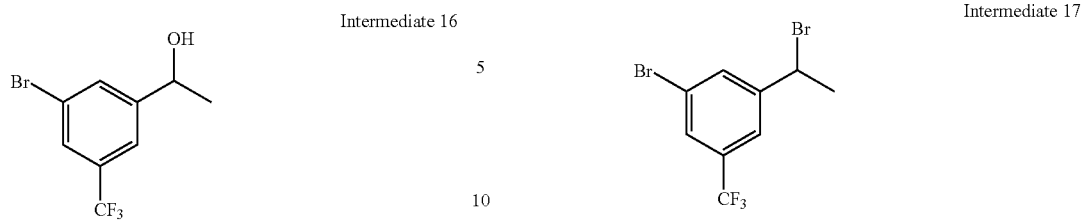

Intermediate 16

Intermediate 17

1-(3-bromo-5-(trifluoromethyl)phenyl)ethanol. To a solution of 1-(3-bromo-5-(trifluoromethyl)phenyl)ethanone (985 mg, 3.68 mmol) in EtOH (5.5 mL) at 0° C., was added sodium borohydride (139 mg, 3.68 mmol). The ice bath was removed and the mixture was stirred at room temperature for 1.5 hours then re-cooled to 0° C. and quenched slowly with saturated aqueous NH$_4$Cl solution. The crude mixture was concentrated under vacuum and the resulting residue was suspended in H$_2$O and extracted with EtOAc. The EtOAc layer was washed with brine, dried over MgSO$_4$, filtered and concentrated under vacuum. Column chromatography on silica gel (5-20% ethyl acetate/hexanes) afforded intermediate 16 (884 mg, 3.28 mmol, 89%). $^1$H NMR (400 MHz, CHLOROFORM-D) δ ppm 1.50 (d, J=6.55 Hz, 3H) 4.93 (q, J=6.55 Hz, 1H) 7.56 (s, 1H) 7.65 (s, 1H) 7.71 (s, 1H). Mass spec.: 270.06 (MH)$^+$.

1-bromo-3-(1-bromoethyl)-5-(trifluoromethyl)benzene. To a solution of 1-(3-bromo-5-(trifluoromethyl)phenyl)ethanol (884 mg, 3.28 mmol) and carbon tetrabromide (1.30 g, 3.94 mmol) in THF (4 mL) at 0° C., was added triphenylphosphine (1.03 g, 3.94 mmol). The mixture was stirred at room temperature for 3 hours then diluted with hexanes and filtered to remove undissolved solids. The organics were concentrated under vacuum. Column chromatography on silica gel (0-15% ethyl acetate/hexanes) afforded intermediate 17 (1.30 g, 3.92 mmol, >100%). $^1$H NMR (400 MHz, CHLOROFORM-D) δ ppm 1.93-2.11 (m, 3H) 5.11 (q, J=6.80 Hz, 1H) 7.59 (s, 1H) 7.67 (s, 1H) 7.75 (s, 1H). Mass spec.: 332.96 (MH$^+$)$^+$.

Table 5 describes compounds that were prepared from 1-bromo-3-(1-bromoethyl)-5-(trifluoromethyl)benzene by following the experimental conditions described for the intermediates (4-13) and examples (1 and 17). Retention time (t$_R$) is in min.

TABLE 5

| Example | Structure | MS (MH)$^+$ | $^1$H NMR |
|---|---|---|---|
| 27 | 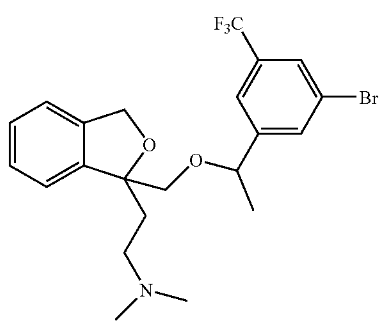 | 473.34 | $^1$H NMR (400 MHz, MeOD) δ ppm 1.29-1.38 (m, 3 H) 1.90 (s, 1 H) 2.12-2.35 (m, 2 H) 2.51-2.62 (m, 6 H) 2.77-2.92 (m, 1 H) 3.38-3.44 (m, 1 H) 3.54-3.63 (m, 1 H) 4.49 (q, J = 6.46 Hz, 1 H) 5.01-5.12 (m, 2 H) 7.20-7.28 (m, 2 H) 7.30-7.37 (m, 2 H) 7.42-7.51 (m, 1 H) 7.56-7.73 (m, 2 H) |
| 28 | 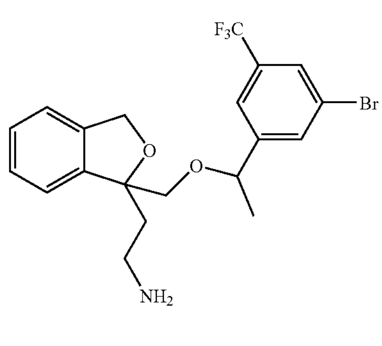 | 445.29 | $^1$H NMR (400 MHz, MeOD) δ ppm 1.20-1.37 (m, 3 H) 1.90-2.20 (m, 2 H) 2.33-2.51 (m, 1 H) 2.55-2.72 (m, 1 H) 3.40 (dd, J = 9.69, 1.13 Hz, 1 H) 3.55 (d, J = 9.82 Hz, 1 H) 4.40-4.55 (m, 1 H) 4.97-5.15 (m, 2 H) 7.12-7.18 (m, 1 H) 7.20-7.34 (m, 3 H) 7.45 (d, J = 18.38 Hz, 1 H) 7.51-7.71 (m, 2 H) |

TABLE 5-continued

| Example | Structure | MS (MH)+ | 1H NMR |
|---|---|---|---|
| 29 | 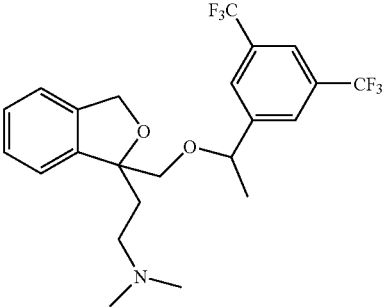 | 462.44 | 1H NMR (400 MHz, MeOD) δ ppm 1.31-1.42 (m, 3 H) 2.26 (s, 2 H) 2.39-2.53 (m, 6 H) 2.76 (s, 1 H) 3.37-3.49 (m, 2 H) 3.58-3.69 (m, 1 H) 4.52-4.70 (m, 1 H) 5.00-5.14 (m, 2 H) 7.18-7.36 (m, 4 H) 7.77 (d, J = 10.83 Hz, 3 H) |
| 30 | 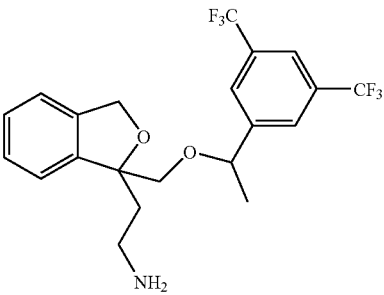 | 434.39 | 1H NMR (400 MHz, MeOD) δ ppm 1.35 (dd, J = 8.31, 6.55 Hz, 3 H) 2.00-2.23 (m, 2 H) 2.49 (s, 1 H) 2.67 (s, 1 H) 3.41 (d, J = 9.57 Hz, 1 H) 3.60 (d, J = 9.82 Hz, 1 H) 4.48-4.72 (m, 1 H) 4.97-5.13 (m, 2 H) 7.12-7.35 (m, 4 H) 7.68-7.84 (m, 3 H) |

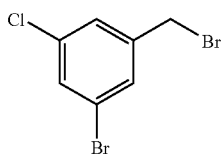

Intermediate 18

1-bromo-3-(bromomethyl)-5-chlorobenzene. To a solution of 3-bromo-5-chloro-benzyl alcohol (1 g, 4.51 mmol) in THF (25 mL) at 0° C., was added N-bromosuccinimide (1.68 g, 9.48 mmol) and triphenylphosphine (2.36 g, 9.03 mmol). The mixture was allowed to stir at room temperature for 3 hours then quenched with saturated NaHCO₃ and extracted with ether. The organic layer was dried over MgSO₄, filtered and concentrated under vacuum. Column chromatography on silica gel (0-5% EtOAc/hexanes) afforded intermediate 18 (1.31 g, 2.68 mmol, >100%). $^1$H NMR (400 MHz, CHLOROFORM-D) δ ppm 4.36 (s, 2H) 7.31 (t, J=1.64 Hz, 1H) 7.40-7.46 (m, 2H). Mass spec.: 285.38 (MH+)+.

Table 6 describes compounds that were prepared from 1-bromo-3-(bromomethyl)-5-chlorobenzene by following the experimental conditions described for the intermediates (4-14) and examples (1, 2 and 17). Retention time ($t_R$) is in min.

TABLE 6

| Example | Structure | MS (MH)+ | 1H NMR |
|---|---|---|---|
| 31 | 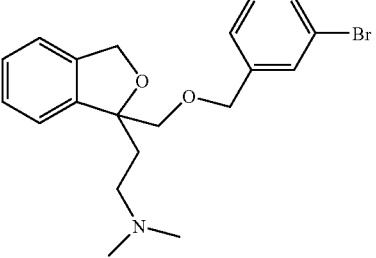 | 425.76 | 1H NMR (400 MHz, MeOD) δ ppm 2.01 (d, J = 6.55 Hz, 1 H) 2.09-2.17 (m, 6 H) 2.28-2.43 (m, 1 H) 3.26-3.33 (m, 2 H) 3.56 (s, 2 H) 4.29-4.49 (m, 2 H) 5.02 (d, J = 5.79 Hz, 2 H) 7.12 (s, 1 H) 7.16-7.22 (m, 2 H) 7.23-7.29 (m, 3 H) 7.38 (t, J = 1.89 Hz, 1 H) |

TABLE 6-continued

| Example | Structure | MS (MH)+ | 1H NMR |
|---|---|---|---|
| 32 | 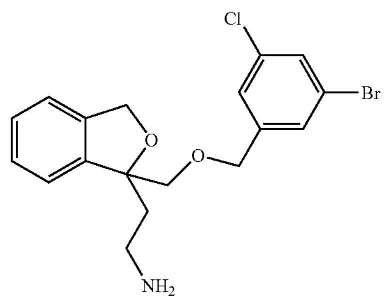 | 497.71 | 1H NMR (400 MHz, MeOD) δ ppm 1.91-2.16 (m, 2 H) 2.32-2.45 (m, 1 H) 2.54-2.67 (m, 1 H) 3.56 (s, 2 H) 4.27-4.47 (m, 2 H) 4.94-5.15 (m, 2 H) 7.11 (s, 1 H) 7.15-7.23 (m, 3 H) 7.23-7.28 (m, 2 H) 7.37 (t, J = 1.89 Hz, 1 H) |
| 33 | 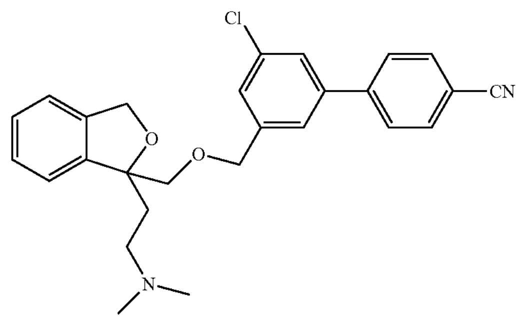 | 447.9 | 1H NMR (400 MHz, MeOD) δ ppm 1.98-2.17 (m, 3 H) 2.21 (s, 6 H) 2.46 (d, J = 11.83 Hz, 1 H) 3.61 (s, 2 H) 4.33-4.64 (m, 2 H) 4.96-5.13 (m, 2 H) 7.16-7.28 (m, 5 H) 7.35 (s, 1 H) 7.52 (t, J = 1.76 Hz, 1 H) 7.65-7.69 (m, 2 H) 7.71-7.77 (m, 2 H) |
| 34 | 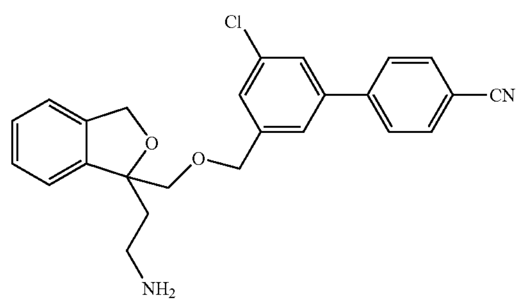 | 419.92 | 1H NMR (400 MHz, MeOD) δ ppm 1.93-2.17 (m, 2 H) 2.30-2.49 (m, 1 H) 2.52-2.72 (m, 1 H) 3.60 (s, 2 H) 4.40-4.59 (m, 2 H) 4.97-5.12 (m, 2 H) 7.16-7.28 (m, 5 H) 7.33 (s, 1 H) 7.51 (t, J = 1.76 Hz, 1 H) 7.64-7.69 (m, 2 H) 7.73-7.77 (m, 2 H) |

Intermediate 19

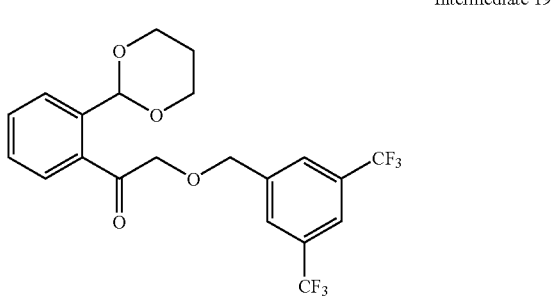

1-(2-(1,3-Dioxan-2-yl)phenyl)-2-(3,5-bis(trifluoromethyl)benzyloxy)ethanone. To a solution of 2-(3,5-bis(trifluoromethyl)benzyloxy)-N-methoxy-N-methylacetamide (5.0 g, 14 mmol) in tetrahydrofuran (20 mL, 247 mmol) at −78° C. was added (2-(1,3-dioxan-2-yl)phenyl)magnesium bromide (0.25M in tetrahydrofuran) (64 mL). The ice bath was replaced with a 0° C. bath and stirring continued for 1 h. The reaction was quenched by addition of saturated ammonium chloride. The mixture was diluted with pentane and the layers separated. The organics were washed with water, then brine, dried over magnesium sulfate, and concentrated. Flash chromatography (12% EtOAc/Hex) gave 3.20 g (49%) as a white crystalline solid. 1H-NMR (CDCl3, 300 MHz) δ 7.80 (s, 2H), 7.78 (s, 1H), 7.70 (d, J=7.6 Hz, 1H), 7.44 (m, 1H), 7.33 (m, 2H), 5.87 (s, 1H), 4.70 (s, 2H), 4.61 (s, 2H), 4.16 (dd, J=11.3, 4.9 Hz, 2H), 3.92 (m, 2H), 2.11 (m, 1H), 1.38 (d, J=13.7 Hz, 1H); 13C-NMR (CDCl3, 126 MHz) δ 202.2, 140.7, 136.9, 136.1, 131.7 (q, J=33.6 Hz), 130.9, 128.4, 127.7, 126.7, 123.4 (q, J=273 Hz), 121.7, 98.7, 75.2, 71.6, 67.4, 25.7.

Intermediate 20

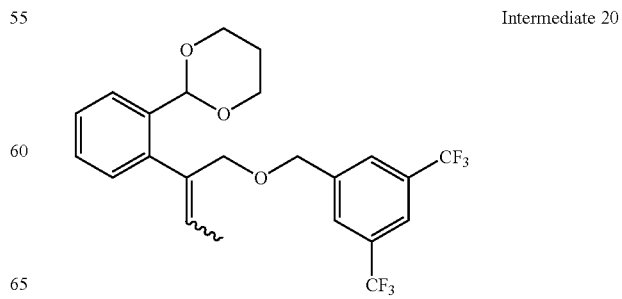

2-(2-(1-(3,5-Bis(trifluoromethyl)benzyloxy)but-2-en-2-yl)phenyl)-1,3-dioxane. To a suspension of ethyl triphenylphosphonium bromide (7.62 g, 20.5 mmol) in tetrahydrofuran (40 mL) at −78° C. was added n-butyllithium (1.6 M in hexane, 12.8 mL, 20.5 mmol). The resulting suspension was warmed to 0° C., stirred 30 min, and cooled to −78° C. The reaction was treated with 1-(2-(1,3-dioxan-2-yl)phenyl)-2-(3,5-bis(trifluoromethyl)benzyloxy)ethanone (2.80 g, 6.25 mmol) as a solid. The reaction was placed in a 0° C. bath and stirred for 30 min. The reaction was stirred at room temperature for 1 h, and quenched by addition of saturated ammonium chloride. The mixture was extracted with ether, which was washed with water (2×), then brine, dried over magnesium sulfate, and concentrated. The reaction was purified by flash chromatography (5-->20% EtOAc/Hex) to give 1.78 g (62%). Mass spec.: 483.13 (MNa)$^+$.

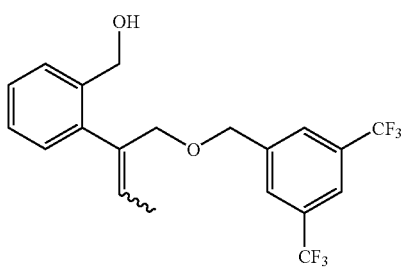

Intermediate 21

(2-(1-(3,5-Bis(trifluoromethyl)benzyloxy)but-2-en-2-yl)phenyl)methanol. To a solution of 2-(2-(1-(3,5-bis(trifluoromethyl)benzyloxy)but-2-en-2-yl)phenyl)-1,3-dioxane (1.75 g, 3.8 mmol) in acetone (100 mL) and water (5 mL) at room temperature was added concentrated hydrochloric acid (0.4 mL). The resulting solution was stirred for 1.5 h. The reaction was quenched by the addition of saturated sodium bicarbonate, and poured into pentane. The organics were washed with water (2×), then brine, dried over magnesium sulfate, and concentrated. The crude residue was dissolved in ethanol (20 mL), cooled to 0° C., and treated with sodium borohydride (0.14 g, 3.8 mmol). After 5 min, the ice bath was removed and stirring continued for 30 min. The mixture was recooled to 0° C., and quenched by addition of saturated ammonium chloride. The mixture was extracted with ether, washed with water (2×), then brine, dried over magnesium sulfate, and concentrated. Column chromatography (5%-->25% EtOAc/Hex) gave 1.22 g (79%) as colorless oil and as a mixture of E- and Z-isomers. $^1$H-NMR (mixture, CDCl$_3$, 300 MHz) δ 7.76 (s, 1H), 7.62 (s, 1.5H), 7.59 (s, 0.4H), 7.20-7.50 (m, 3.3H), 7.13 (d, J=7.0 Hz, 0.2H), 7.05 (m, 0.8H), 5.96 (q, J=6.7 Hz, 0.8H), 5.72 (q, J=7.0 Hz, 0.2H), 4.05-4.80 (m, 6.2H), 2.65 (m, 1H), 1.85 (d, J=7.0 Hz, 0.6H), 1.66 (bs, 0.4H), 1.47 (d, J=6.7 Hz, 2.4H).

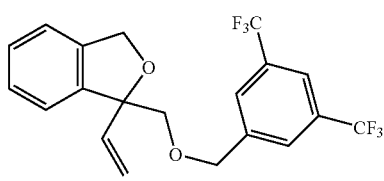

Intermediate 22

1-((3,5-Bis(trifluoromethyl)benzyloxy)methyl)-1-vinyl-1,3-dihydroisobenzofuran. A flask was charged with (2-(1-(3,5-bis(trifluoromethyl)benzyloxy)but-2-en-2-yl)phenyl)methanol (1.22 g, 3.0 mmol), palladium trifluoroacetate (50.2 mg, 0.15 mmol), pyridine (0.049 mL, 0.60 mmol), sodium carbonate (160 mg, 1.5 mmol), molecular sieves (3 A, 1.5 g), and toluene (16 mL). The mixture was stirred under a balloon of oxygen, and was heated at 80° C. for 3 h. The reaction was cooled to room temperature, diluted with ether, and filtered through celite. The organics were washed with water (2×), then brine, dried over magnesium sulfate, and concentrated. To aid in separation of the aldehyde byproduct (via oxidation of the alcohol), the following procedure was used to convert it back to starting material. The crude mixture was dissolved in ethanol (6 mL) and treated with sodium borohydride (30 mg, 0.79 mmol). The mixture was stirred at room temperature for 10 min. The mixture was cooled to 0° C., quenched by addition of saturated ammonium chloride, diluted with ether, washed with water (2×), then brine, dried over magnesium sulfate, and concentrated. Column chromatography (2.5%-->30% EtOAc/Hex) gave 828 mg (68%) as a colorless oil. $^1$H-NMR (CDCl$_3$, 300 MHz) δ 7.79 (s, 1H), 7.70 (s, 2H), 7.33 (m, 2H), 7.25 (m, 2H), 6.17 (dd, J=17.1, 10.7 Hz, 1H), 5.44 (dd, J=17.1, 1.5 Hz, 1H), 5.24 (dd, J=10.7, 1.2 Hz, 1H), 5.20 (q$_{AB}$, J$_{AB}$=12.2 Hz, 2H), 4.70 (q$_{AB}$, J$_{AB}$=13.4 Hz, 2H), 3.83 (q$_{AB}$, J$_{AB}$=10.4 Hz, 2H); $^{13}$C-NMR (CDCl$_3$, 126 MHz) δ 141.4, 141.0, 139.6, 138.2, 131.7 (q, J=33.6 Hz), 128.2, 127.5, 127.2, 123.5 (q, J=273 Hz), 121.9, 121.4, 121.3, 115.0, 90.1, 76.1, 72.4, 72.0. Mass spec.: 425.12 (MNa)$^+$.

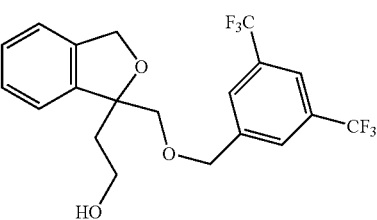

Intermediate 23

2-(1-((3,5-Bis(trifluoromethyl)benzyloxy)methyl)-1,3-dihydroisobenzofuran-1-yl)ethanol. 1-((3,5-Bis(trifluoromethyl)benzyloxy)methyl)-1-vinyl-1,3-dihydroisobenzofuran (775 mg, 1.93 mmol) was dissolved in 9-BBN (0.5 M in tetrahydrofuran, 13.5 mL, 6.75 mmol) and stirred at room temperature for 5 h. The reaction was quenched by addition of water (1 mL), cooled to 0° C., treated with 4 M sodium hydroxide (6 mL) and 30% hydrogen peroxide (6 mL), and stirred at 0° C. for 1 h. The reaction was quenched by addition of saturated ammonium chloride, extracted with ethyl acetate (2×). The organics were washed with sodium bicarbonate, then brine, dried over magnesium sulfate, and concentrated. Column chromatography (12%-->37% EtOAc/Hex) gave 650 mg (80%) as a colorless oil. $^1$H-NMR (CDCl$_3$, 300 MHz) δ 7.76 (s, 1H), 7.63 (s, 2H), 7.32 (m, 2H), 7.25 (m, 1H), 7.15 (d, J=6.7 Hz, 1H), 5.15 (q$_{AB}$, J$_{AB}$=120.5 Hz, 2H), 4.62 (q$_{AB}$, J$_{AB}$=13.1 Hz, 2H), 3.69 (q$_{AB}$, J$_{AB}$=10.1 Hz, 2H), 2.59 (bs, 1H), 2.31 (ddd, J=14.7, 7.6, 4.6 Hz, 1H), 2.11 (ddd, J=14.7, 6.4, 4.3 Hz, 1H); $^{13}$C-NMR (CDCl$_3$, 126 MHz) δ 141.2, 141.1, 139.7, 131.8 (q, J=33.6 Hz), 128.4, 127.8, 127.1, 123.4 (q, J=273 Hz), 121.7, 121.5, 121.2, 90.9, 76.4, 72.7, 72.0, 59.3, 38.3. Mass spec.: 421.13 (MH)$^+$.

Intermediate 24

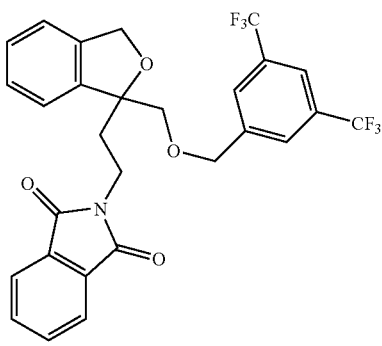

2-(2-(1-((3,5-Bis(trifluoromethyl)benzyloxy)methyl)-1,3-dihydroisobenzofuran-1-yl)ethyl)isoindoline-1,3-dione.
To a solution of 2-(1-((3,5-bis(trifluoromethyl)benzyloxy)methyl)-1,3-dihydroisobenzofuran-1-yl)ethanol (200 mg, 0.48 mmol), isoindoline-1,3-dione (105 mg, 0.71 mmol), and triphenylphosphine (187 mg, 0.71 mmol) in tetrahydrofuran (5 mL) at 0° C. was added diethyl azodicarboxylate (0.112 mL, 0.71 mmol). The ice bath was removed and stirring continued for 1 h. Clean, complete conversion to product was observed. The reaction was quenched by addition of saturated ammonium chloride, and extracted with ethyl acetate (2×). The organics were washed with water, then saturated sodium bicarbonate, then brine, dried over magnesium sulfate, and concentrated. Column chromatography (8% EtOAc/Hex-->12% EtOAc/Hex) gave 255 mg (98%) as a colorless oil. $^1$H-NMR (CDCl$_3$, 300 MHz) δ 7.73 (s, 1H), 7.67 (m, 2H), 7.63 (s, 2H), 7.61 (m, 2H), 7.00-7.15 (m, 4H), 5.16 (q$_{AB}$, J$_{AB}$=12.2 Hz, 2H), 4.60 (s, 2H), 3.77 (m, 1H), 3.68 (m, 1H), 3.63 (s, 2H), 2.47 (m, 1H), 2.30 (ddd, J=14.4, 7.3, 4.9 Hz, 1H); $^{13}$C-NMR (CDCl$_3$, 126 MHz) δ 168.1, 141.2, 140.6, 140.0, 133.7, 132.2, 131.7 (q, J=33.6 Hz), 128.0, 127.4, 127.2, 123.4 (q, J=273 Hz), 122.9, 121.5, 121.4, 121.2, 88.9, 76.8, 73.0, 72.0, 33.6, 33.5. Mass spec.: 550.20 (MH)$^+$.

EXAMPLE 35

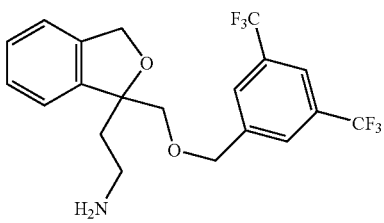

2-(1-((3,5-Bis(trifluoromethyl)benzyloxy)methyl)-1,3-dihydroisobenzofuran-1-yl)ethanamine. To a solution of 2-(2-(1-((3,5-bis(trifluoromethyl)benzyloxy)methyl)-1,3-dihydroisobenzofuran-1-yl)ethyl)isoindoline-1,3-dione (250 mg, 0.455 mmol) in ethanol (2 mL) was added hydrazine (0.100 mL, 3.2 mmol). The resulting solution was heated to 45° C. and held there for 3 h. The reaction was cooled to room temperature, diluted with ether, and filtered to remove the precipitate which was discarded. Concentration of the mother liquor gave 175 mg (92%) as a colorless oil. $^1$H-NMR (CDCl$_3$, 300 MHz) δ 7.74 (s, 1H), 7.63 (s, 2H), 7.28 (m, 2H), 7.21 (m, 1H), 7.16 (m, 1H), 5.11 (s, 2H), 4.61 (q$_{AB}$, J$_{AB}$=12.8 Hz, 2H), 3.65 (q$_{AB}$, J$_{AB}$=9.8 Hz, 2H), 2.73 (m, 1H), 2.54 (m, 1H), 2.13 (ddd, J=14.4, 8.6, 5.8 Hz, 1H), 2.00 (ddd, J=14.3, 8.6, 5.8 Hz, 1H), 1.55 (bs, 2H); $^{13}$C-NMR (CDCl$_3$, 126 MHz) δ 141.4, 141.3, 139.9, 131.7 (q, J=33.6 Hz), 128.2, 127.5, 127.1, 123.4 (q, J=273 Hz), 121.7, 121.4, 121.1, 90.0, 76.8, 72.8, 72.0, 40.4, 37.4. Mass spec.: 420.14 (MH)$^+$. Accurate mass spec.: m/z 420.1391 [MH]$^+$, Δ=1.7 ppm.

EXAMPLE 36

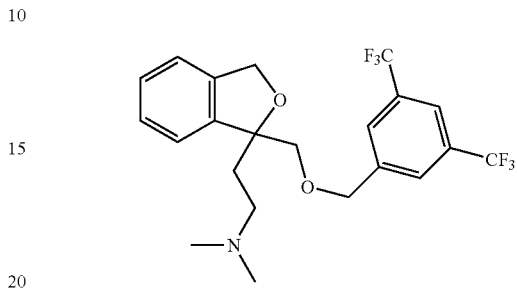

2-(1-((3,5-Bis(trifluoromethyl)benzyloxy)methyl)-1,3-dihydroisobenzofuran-1-yl)-N,N-dimethylethanamine. To a solution of 2-(1-((3,5-bis(trifluoromethyl)benzyloxy)methyl)-1,3-dihydroisobenzofuran-1-yl)ethanamine (40 mg, 95.4 μmol) in acetonitrile (2 mL) at 0° C. was added formalin (0.250 mL) and then sodium cyanoborohydride (30 mg, 0.48 mmol). The ice bath was removed and stirring continued for 1 h, occasionally treating with a drop of acetic acid to keep the pH slightly less than 7. The reaction was concentrated, diluted with ether, washed with 1 M sodium hydroxide, then brine, dried over sodium sulfate, and concentrated. Column chromatography (4% MeOH/DCM) gave 28.5 mg (67%) as a colorless oil. $^1$H-NMR (CDCl$_3$, 300 MHz) δ 7.75 (s, 1H), 7.64 (s, 2H), 7.30 (m, 2H), 7.15-7.25 (m, 2H), 5.11 (q$_{AB}$, J$_{AB}$=120.5 Hz, 2H), 4.62 (q$_{AB}$, J$_{AB}$=13.4 Hz, 2H), 3.67 (q$_{AB}$, J$_{AB}$=10.1 Hz, 2H), 2.41 (ddd, J=11.3, 11.3, 5.5 Hz, 1H), 2.20 (s, 6H), 2.19 (m, 1H), 1.98-2.14 (m, 2H); $^{13}$C-NMR (CDCl$_3$, 126 MHz) δ 141.3, 141.2, 139.9, 131.7 (q, J=33.6 Hz), 128.2, 127.6, 126.1, 123.4 (q, J=273 Hz), 121.6, 121.4, 121.1, 89.5, 76.8, 72.9, 72.0, 54.3, 45.4, 34.4. Mass spec.: 448.22 (MH)$^+$. Accurate mass spec.: m/z 448.1711 [MH]$^+$, Δ=0.6 ppm.

Intermediate 25

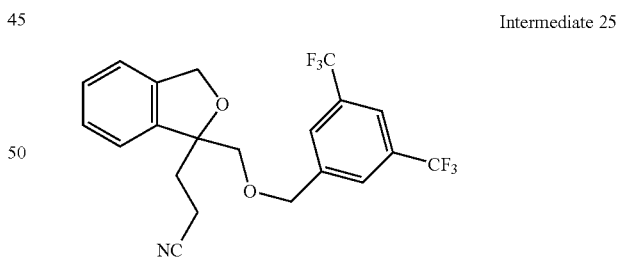

3-(1-((3,5-Bis(trifluoromethyl)benzyloxy)methyl)-1,3-dihydroisobenzofuran-1-yl)propanenitrile. To a solution of 2-(1-((3,5-bis(trifluoromethyl)benzyloxy)methyl)-1,3-dihydroisobenzofuran-1-yl)ethanol (250 mg, 0.60 mmol) and triphenylphosphine (390 mg, 1.5 mmol) in tetrahydrofuran (2.5 mL) at 0° C. was added acetone cyanohydrin (0.163 mL, 1.8 mmol), followed immediately by the addition of diethyl azodicarboxylate (0.234 mL, 1.5 mmol). The reaction was allowed to gradually warm to room temperature in the dewar overnight. The reaction was diluted with ether, washed with water, then saturated sodium bicarbonate, then water, then brine, dried over magnesium sulfate, and concentrated. Column chromatography (12%-->19% EtOAc/Hex) gave 214 mg (84%) as a colorless oil. $^1$H-NMR (CDCl$_3$, 300 MHz) δ 7.77 (s, 1H), 7.66 (s, 2H), 7.35 (m, 2H), 7.25 (m, 1H), 7.18 (d, J=6.7 Hz, 1H), 5.14 (s, 2H), 4.64 (s, 2H), 3.65 (s, 2H), 2.38 (m, 2H), 2.22 (m, 1H), 2.07 (m, 1H); $^{13}$C-NMR (CDCl$_3$, 126 MHz) δ 140.9, 140.0, 139.4, 131.8 (q, J=33.6 Hz), 128.9, 128.0, 127.2, 123.4 (q, J=273 Hz), 121.7, 121.6, 121.5, 119.7, 88.9, 76.2, 73.1, 72.1, 32.4, 11.8. Mass spec.: 430.09 (MH)$^+$.

EXAMPLE 37

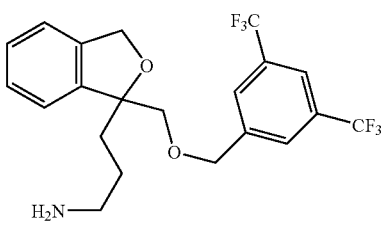

3-(1-((3,5-Bis(trifluoromethyl)benzyloxy)methyl)-1,3-dihydroisobenzofuran-1-yl)propan-1-amine. To a solution of 3-(1-((3,5-bis(trifluoromethyl)benzyloxy)methyl)-1,3-dihydroisobenzofuran-1-yl)propanenitrile (190 mg, 0.44 mmol) and nickel(II) chloride hexahydrate (158 mg, 0.66 mmol) in methanol (4 mL) at 0° C. was added sodium borohydride (117 mg, 3.1 mmol) in several portions over 30 minutes. The ice bath was removed and stirring continued for 1 h. Very clean and mostly complete conversion to product (by LC/MS) was observed. The reaction was cooled to 0° C. and treated with concentrated hydrochloric acid (85 μL). After 5 min, celite was added, and the mixture was filtered. The solution was made basic by addition of solid sodium bicarbonate, and filtered again. The organics were concentrated to give the crude amine which was purified by column chromatography (10% MeOH/DCM-->10:90:0.5 MeOH/DCM/Me$_3$N in EtOH) to give 114 mg (59%) as a colorless oil. $^1$H-NMR (CDCl$_3$, 300 MHz) δ 7.73 (s, 1H), 7.63 (s, 2H), 7.05-7.40 (m, 4H), 5.11 (s, 2H), 4.61 (q$_{AB}$, J$_{AB}$=13.1 Hz, 2H), 3.66 (s, 2H), 2.64 (m, 2H), 1.70-2.10 (m, 4H), 1.50 (m, 1H), 1.20 (m, 1H); $^{13}$C-NMR (CDCl$_3$, 126 MHz) δ 141.42, 141.39, 140.1, 131.7 (q, J=33.6 Hz), 128.1, 127.5, 127.1, 123.4 (q, J=273 Hz), 121.6, 121.4, 121.1, 90.3, 76.8, 72.9, 72.0, 42.3, 34.1, 27.3. Mass spec.: 434.25 (MH)$^+$. Accurate mass spec.: m/z 434.1542 [MH]$^+$, Δ=1.3 ppm.

EXAMPLE 38

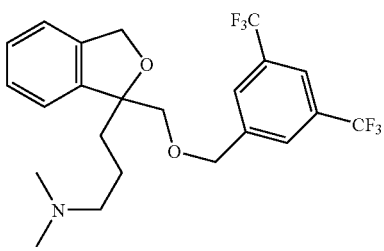

3-(1-((3,5-is(trifluoromethyl)benzyloxy)methyl)-1,3-dihydroisobenzofuran-1-yl)-N,N-dimethylpropan-1-amine. To a solution of 3-(1-((3,5-bis(trifluoromethyl)benzyloxy)me-thyl)-1,3-dihydroisobenzofuran-1-yl)propan-1-amine (40 mg, 92.3 μmol) in acetonitrile (2 mL) at 0° C. was added formalin (0.250 mL) and then sodium cyanoborohydride (29 mg, 0.46 mmol). The ice bath was removed and stirring continued for 1 h, occasionally treating with a drop of acetic acid to keep the pH slightly less than 7. The reaction was diluted with ether, washed with 1 M sodium hydroxide, then brine, dried over sodium sulfate, and concentrated. Column chromatography (4% MeOH/DCM) gave 27.5 mg (65%) as a colorless oil. $^1$H-NMR (CDCl$_3$, 300 MHz) δ 7.74 (s, 1H), 7.63 (s, 2H), 7.29 (m, 2H), 7.21 (m, 1H), 7.15 (m, 1H), 5.13 (s, 2H), 4.61 (q$_{AB}$, J$_{AB}$=13.1 Hz, 2H), 3.67 (s, 2H), 2.28 (m, 2H), 2.18 (s, 6H), 1.95 (m, 1H), 1.86 (m, 1H), 1.54 (m, 1H), 1.24 (m, 1H); $^{13}$C-NMR (CDCl$_3$, 126 MHz) δ 141.42, 141.39, 140.1, 131.7 (q, J=33.6 Hz), 128.1, 127.5, 127.12, 127.10, 123.4 (q, J=273 Hz), 121.6, 121.4, 121.1, 90.4, 73.0, 72.0, 59.8, 45.2, 34.4, 21.4. Mass spec.: 462.26 (MH)$^+$. Accurate mass spec.: m/z 462.1868 [MH]$^+$, Δ=0.1 ppm.

Intermediate 27

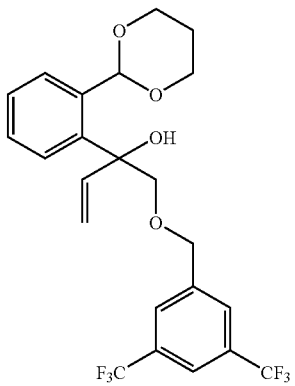

2-(2-(1,3-Dioxan-2-yl)phenyl)-1-(3,5-bis(trifluoromethyl)benzyloxy)but-3-en-2-ol. To a solution of 1-(2-(1,3-dioxan-2-yl)phenyl)-2-(3,5-bis(trifluoromethyl)benzyloxy) ethanone (1.06 g, 2.36 mmol) in tetrahydrofuran (15 mL) at −78° C. was added vinylmagnesium bromide (1 M in tetrahydrofuran, 4.73 mL, 4.73 mmol). The reaction was allowed to warm to −60° C. in the Dewar flask before quenching with saturated ammonium chloride. The reaction was poured into diethyl ether, washed with water, then brine, dried over magnesium sulfate, and concentrated. Column chromatography (12%-->25% EtOAc/Hex) gave 810 mg (72%) as a colorless oil. Mass spec.: 499.30 (MNa)$^+$.

Intermediate 28

3-((3,5-Bis(trifluoromethyl)benzyloxy)methyl)-3-vinyl-1,3-dihydroisobenzofuran-1-ol. To a solution of 2-(2-(1,3- dioxan-2-yl)phenyl)-1-(3,5-bis(trifluoromethyl)benzyloxy) but-3-en-2-ol (800 mg, 1.68 mmol) in acetone (20 mL) and water (1 mL) was added concentrated hydrochloric acid (0.2 mL) at room temperature. The resulting reaction was stirred at room temperature for 2 h. The reaction was quenched by addition of saturated sodium bicarbonate, and concentrated to remove most of the acetone. The mixture was poured into diethyl ether, washed with water, then brine, dried over magnesium sulfate, and concentrated. Column chromatography (25%-->50% EtOAc/Hex) gave 475 mg (68%) as a colorless oil. Mass spec.: 401.32 (M-OH)$^+$.

Intermediate 29

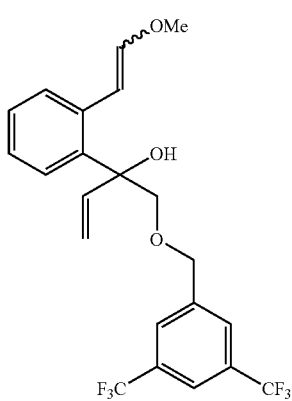

1-(3,5-Bis(trifluoromethyl)benzyloxy)-2-(2-(2-methoxyvinyl)phenyl)but-3-en-2-ol. To a suspension of 3-((3,5-bis(trifluoromethyl)benzyloxy)methyl)-3-vinyl-1,3-dihydroisobenzofuran-1-ol (475 mg, 1.14 mmol) and (methoxymethyl)triphenylphosphonium chloride (973 mg, 2.84 mmol) in tetrahydrofuran (6 mL) at 0° C. was added potassium tert-butoxide (319 mg, 2.84 mmol). The ice bath was removed and stirring continued for 6 h. The reaction was quenched by addition of saturated ammonium chloride and poured into diethyl ether. The ethereal was washed with water, then brine, dried over magnesium sulfate, and concentrated. Column chromatography (12%-->25% EtOAc/Hex) gave 210 mg (41%) as a colorless oil. Mass spec.: 469.23 (MNa)$^+$.

Intrmediate 30

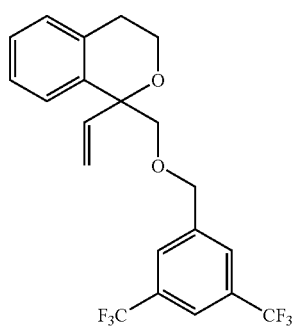

1-((3,5-Bis(trifluoromethyl)benzyloxy)methyl)-1-vinylisochroman. To a solution of 1-(3,5-bis(trifluoromethyl)benzyloxy)-2-(2-(2-methoxyvinyl)phenyl)but-3-en-2-ol (190 mg, 0.426 mmol) and triethylsilane (0.27 mL, 1.7 mmol) in dichloromethane (4 mL) at −78° C. was added boron trifluoride etherate (0.11 mL, 0.85 mmol) dropwise. The ice bath was removed after 10 min, stirred at room temperature for 30 min, recooled to −78° C., and quenched by addition of saturated sodium bicarbonate. The mixture was extracted with diethyl ether (2×) which was washed with brine, dried over magnesium sulfate, and concentrated. Column chromatography (3%-->10% EtOAc/Hex) gave 125 mg (71%). $^1$H-NMR (CDCl$_3$, 300 MHz) δ 7.74 (s, 1H), 7.64 (s, 2H), 7.20 (m, 2H), 7.13 (m, 2H), 6.04 (dd, J=17.1, 10.7 Hz, 1H), 5.31 (dd, J=10.7, 1.2 Hz, 1H), 5.20 (dd, J=17.4, 1.5 Hz, 1H), 4.67 (q$_{AB}$, J$_{AB}$=13.4 Hz, 2H), 4.04 (ddd, J=11.3, 5.5, 2.4 Hz, 1H), 3.87 (ddd, J=11.0, 11.0, 3.4 Hz, 1H), 3.79 (q$_{AB}$, J$_{AB}$=10.4 Hz, 2H), 3.04 (ddd, J=16.5, 11.0, 5.8 Hz, 1H), 2.64 (ddd, J=16.2, 2.7, 2.7 Hz, 1H); $^{13}$C-NMR (CDCl$_3$, 126 MHz) δ 141.4, 139.1, 135.9, 135.2, 131.6 (q, J=33.6 Hz), 129.2, 127.3, 126.9, 126.4, 126.0, 123.5 (q, J=273 Hz), 121.4, 117.4, 80.0, 77.6, 72.2, 60.3, 29.4. Mass spec.: 439.25 (MNa)$^+$.

Intermediate 31

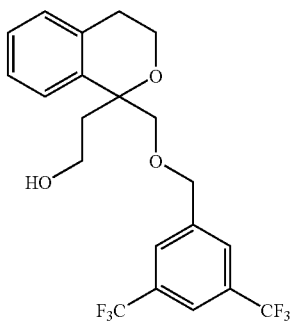

2-(1-((3,5-Bis(trifluoromethyl)benzyloxy)methyl)isochroman-1-yl)ethanol. 1-((3,5-Bis(trifluoromethyl)benzyloxy)methyl)-1-vinylisochroman (125 mg, 0.300 mmol) was dissolved in 9-BBN (0.5 M in tetrahydrofuran, 2.4 mL, 1.2 mmol) and stirred overnight at room temperature. The reaction was cooled to 0° C. and treated with 4 M sodium hydroxide (1 mL) and then 30% hydrogen peroxide (1 mL) dropwise. The reaction was stirred at 0° C. for 1 h and then quenched by addition of saturated ammonium chloride. The mixture was extracted with diethyl ether (2×) which was washed with brine, dried over magnesium sulfate, and purified by column chromatography (25%-->37% EtOAc/Hex) to give 125 mg (96%) as a colorless oil. $^1$H-NMR (CDCl$_3$, 300 MHz) δ 7.77 (s, 1H), 7.70 (s, 2H), 7.05-7.25 (m, 4H), 4.67 (q$_{AB}$, J$_{AB}$=13.1 Hz, 2H), 4.03 (dd, J=7.3, 3.7 Hz, 2H), 3.78 (q$_{AB}$, J$_{AB}$=10.4 Hz, 2H), 3.61 (m, 2H), 2.99 (m, 1H), 2.72 (ddd, J=16.2, 3.4, 3.4 Hz, 1H), 2.62 (bs, 1H), 2.36 (m, 1H), 2.12 (ddd, J=15.0, 5.5, 4.6 Hz, 1H); $^{13}$C-NMR (CDCl$_3$, 126 MHz) δ 141.1, 136.9, 134.8, 131.8 (q, J=33.6 Hz), 129.2, 127.3, 127.1, 126.6, 125.6, 123.4 (q, J=273 Hz), 121.6, 79.9, 76.4, 72.1, 60.7, 59.3, 39.9, 29.5. Mass spec.: 435.29 (MH)$^+$.

Intermediate 32

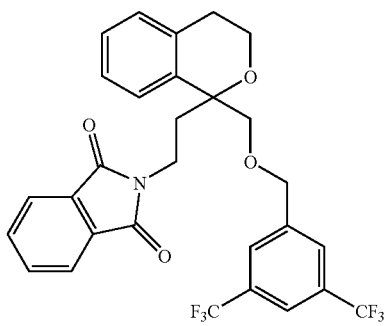

2-(2-(1-((3,5-Bis(trifluoromethyl)benzyloxy)methyl)isochroman-1-yl)ethyl)isoindoline-1,3-dione. To a solution of 2-(1-((3,5-bis(trifluoromethyl)benzyloxy)methyl)isochroman-1-yl)ethanol (100 mg, 0.230 mmol), phthalimide (50.8 mg, 0.345 mmol), and tetrahydrofuran (2 mL) at 0° C. was added diethylazodicarboxylate (0.055 mL, 0.345 mmol) dropwise. The ice bath was removed and stirring continued for 1 h. The reaction was quenched by addition of saturated ammonium chloride and extracted with ethyl acetate (2×) which was washed with brine, dried over magnesium sulfate, and concentrated. Column chromatography (8%-->12% EtOAc/Hex) gave 105 mg (81%) as a colorless oil. $^1$H-NMR (CDCl$_3$, 300 MHz) δ 7.55-7.80 (m, 7H), 7.12 (d, J=7.6 Hz, 1H), 7.01 (m, 3H), 4.66 (q$_{AB}$, J$_{AB}$=13.1 Hz, 2H), 4.03 (m, 2H), 3.74 (m, 2H), 3.72 (q$_{AB}$, J$_{AB}$=10.4 Hz, 2H), 3.02 (m, 1H), 2.66 (m, 1H), 2.30-2.50 (m, 2H); $^{13}$C-NMR (CDCl$_3$, 126 MHz) δ 168.2, 141.2, 136.6, 134.9, 133.7, 132.2, 131.7 (q, J=33.6 Hz), 129.2, 127.4, 126.8, 126.3, 125.5, 123.4 (q, J=273 Hz), 123.0, 121.5, 77.4, 76.1, 72.2, 60.4, 35.5, 33.5, 29.2.

EXAMPLE 39

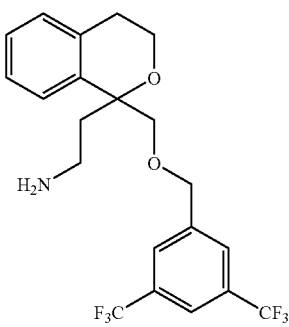

2-(1-((3,5-Bis(trifluoromethyl)benzyloxy)methyl)isochroman-1-yl)ethanamine. To a solution of 2-(2-(1-((3,5-bis(trifluoromethyl)benzyloxy)methyl)isochroman-1-yl)ethyl)isoindoline-1,3-dione (100 mg, 0.177 mmol) in ethanol (1 mL) at room temperature was added hydrazine (0.039 mL, 1.24 mmol). The flask was sealed, heated to 45° C., and held there for 3 h. The reaction was cooled to room temperature, diluted with diethyl ether, and filtered to remove the precipitate which was discarded. The mother liquor was concentrated to give 78 mg (quant.) as a colorless oil. $^1$H-NMR (CDCl$_3$, 300 MHz) δ 7.75 (s, 1H), 7.69 (s, 2H), 7.05-7.20 (m, 2H), 4.64 (q$_{AB}$, J$_{AB}$=13.1 Hz, 2H), 3.99 (m, 2H), 3.71 (q$_{AB}$, J$_{AB}$=10.1 Hz, 2H), 2.91 (m, 1H), 2.76 (m, 1H), 2.68 (m, 1H), 2.50 (m, 1H), 2.16 (m, 1H), 2.02 (m, 1H), 1.79 (bs, 2H); $^{13}$C-NMR (CDCl$_3$, 126 MHz) δ 141.3, 137.3, 135.0, 131.7 (q, J=33.6 Hz), 129.1, 127.3, 126.8, 126.5, 125.6, 123.4 (q, J=273 Hz), 121.5, 78.4, 76.7, 72.1, 60.7, 41.9, 37.3, 29.6. Mass spec.: 434.37 (MH)$^+$. Accurate mass spec.: m/z 434.1547 [MH]$^+$, Δ=1.8 ppm.

EXAMPLE 40

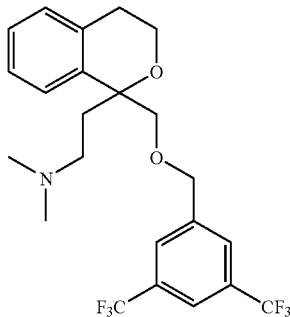

2-(1-((3,5-Bis(trifluoromethyl)benzyloxy)methyl)isochroman-1-yl)-N,N-dimethylethanamine. To a solution of 2-(1-((3,5-bis(trifluoromethyl)benzyloxy)methyl)isochroman-1-yl)ethanamine (25 mg, 0.058 mmol) and sodium cyanoborohydride (18.1 mg, 0.288 mmol) in acetonitrile (1.2 mL) at 0° C. was added formalin (0.15 mL). The ice bath was removed and stirring continued for 1 h, occasionally treating with a small drop of acetic acid to keep the pH slightly less than 7. The reaction was concentrated, dissolved in methanol, and loaded onto an SCX cartridge. The cartridge was flushed with several volumes of methanol which were discarded. The crude product was eluted with 2M ammonia in methanol and concentrated. The product was purified by column chromatography (5%-->10% MeOH/DCM) to give 15 mg (56%) as a colorless film. $^1$H-NMR (CD$_3$OD, 300 MHz) δ 7.84 (m, 3H), 7.08-7.27 (m, 4H), 4.69 (q$_{AB}$, J$_{AB}$=13.1 Hz, 2H), 4.01 (m, 1H), 3.93 (ddd, J=11.3, 5.2, 4.0 Hz, 1H), 3.80 (q$_{AB}$, J$_{AB}$=10.4 Hz, 2H), 2.88 (m, 1H), 2.68 (ddd, J=16.2, 3.7, 3.4 Hz, 1H), 2.50 (m, 1H), 2.22 (m, 1H), 2.18 (s, 6H), 2.00-2.12 (m, 2H); $^{13}$C-NMR (CD$_3$OD, 126 MHz) δ 142.6, 137.3, 135.3, 131.7 (q, J=32.6 Hz), 129.0, 127.5, 126.9, 126.5, 125.6, 123.8 (q, J=272 Hz), 121.0, 78.3, 76.7, 71.7, 60.7, 54.1, 44.3, 35.2, 29.4. Mass spec.: 462.40 (MH)$^+$. Accurate mass spec.: m/z 462.1882 [MH]$^+$, Δ=3.1 ppm.

The invention claimed is:
1. A compound of Formula I

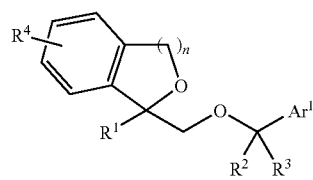

where:
R$^1$ is (R$^5$R$^6$N)alkyl;
R$^2$ is hydrogen or alkyl;
R$^3$ is hydrogen or alkyl;
R$^4$ is hydrogen, halo, alkyl, haloalkyl, or cyano;

R⁵ is hydrogen or alkyl;
R⁶ is hydrogen or alkyl;
or R⁵R⁶N taken together is pyrrolidinyl, piperidinyl, piperazinyl, (alkyl)piperazinyl, morpholinyl, or thiomorpholinyl:
R⁷ is hydrogen or alkyl;
R⁸ is hydrogen or alkyl;
or R⁷R⁸N taken together is pyrrolidinyl, piperidinyl, piperazinyl, (alkyl)piperazinyl, morpholinyl, or thiomorpholinyl:
R⁹ is hydrogen or alkyl;
R¹⁰ is hydrogen or alkyl;
Ar¹ is phenyl substituted with 0-3 substituents selected from the group consisting of halo, alkyl, haloalkyl, hydroxy, alkoxy, haloalkoxy, cyano, NR⁷R⁸, and Ar²;
Ar² is phenyl or pyridinyl and is substituted with 0-3 substituents selected from the group consisting of halo, alkyl, haloalkyl, hydroxy, alkoxy, haloalkoxy, cyano, and CONR⁹R¹⁰; and
n is 1, 2, or 3;
or a pharmaceutically acceptable salt thereof.

2. A compound of claim 1 where R¹ is (R⁵R⁶N)ethyl.
3. A compound of claim 1 where R¹ is (R⁵R⁶N)propyl.
4. A compound of claim 1 where R² and R³ are hydrogen.
5. A compound of claim 1 where R² is methyl and R³ is hydrogen.
6. A compound of claim 1 where R⁴ is hydrogen.
7. A compound of claim 1 where R⁴ is cyano.
8. A compound of claim 1 where Ar¹ is phenyl substituted with 2 substituents selected from the group consisting of halo, alkyl, haloalkyl, hydroxy, alkoxy, haloalkoxy, cyano, NR⁷R⁵ and Ar².
9. A compound of claim 1 where Ar¹ is phenyl substituted with 2 substituents selected from the group consisting of halo, alkyl, haloalkyl, hydroxy, alkoxy, haloalkoxy, cyano, or NR⁷R⁸.
10. A compound of claim 1 where Ar¹ is phenyl substituted with 1 substituent selected the group consisting of halo, alkyl, haloalkyl, hydroxy, alkoxy, haloalkoxy, cyano, and NR⁷R⁸, and is substituted with 1 Ar² substituent.
11. A compound of claim 1 selected from the group consisting of
1-isobenzofuranethanamine, 1-[[[3,5-bis(trifluoromethyl)phenyl]methoxy]methyl]-1,3-dihydro-N,N-dimethyl-;
1-isobenzofuranethanamine, 1-[[[3-bromo-5-(trifluoromethyl)phenyl]methoxy]methyl]-1,3-dihydro-;
[1,1'-biphenyl]-4-carbonitrile, 3'-[[[1-(2-aminoethyl)-1,3-dihydro-1-isobenzofuranyl]methoxy]methyl]-5'-(trifluoromethyl)-;
1-isobenzofuranethanamine, 1-[[[3',4'-difluoro-5-(trifluoromethyl)[1,1'-biphenyl]-3-yl]methoxy]methyl]-1,3-dihydro-;
1-isobenzofuranethanamine, 1-[[[3,5-bis(trifluoromethyl)phenyl]methoxy]methyl]-1,3-dihydro-;
1-isobenzofuranpropanamine, 1-[[[3,5-bis(trifluoromethyl)phenyl]methoxy]methyl]-1,3-dihydro-;
5-isobenzofurancarbonitrile, 1-[[[3,5-bis(trifluoromethyl)phenyl]methoxy]methyl]-1-[2-(dimethylamino)ethyl]-1,3-dihydro-;
5-isobenzofurancarbonitrile, 1-[[[3-bromo-5-(trifluoromethyl)phenyl]methoxy]methyl]-1-[2-(dimethylamino)ethyl]-1,3-dihydro-;
5-isobenzofurancarbonitrile, 1-(2-aminoethyl)-1-[[[3,5-bis(trifluoromethyl)phenyl]methoxy]methyl]-1,3-dihydro-;
5-isobenzofurancarbonitrile, 1-(2-aminoethyl)-1-[[[3-bromo-5-(trifluoromethyl)phenyl]methoxy]methyl]-1,3-dihydro-;
5-isobenzofurancarbonitrile, 1-[[[4'-cyano-5-(trifluoromethyl)[1,1'-biphenyl]-3-yl]methoxy]methyl]-1-[2-(dimethylamino)ethyl]-1,3-dihydro-:
5-isobenzofurancarbonitrile, 1-[2-(dimethylamino)ethyl]-1,3-dihydro-1-[[[3-(4-pyridinyl)-5-(trifluoromethyl)phenyl]methoxy]methyl]-;
1-isobenzofuranethanamine, 1-[[[3-bromo-5-(trifluoromethyl)phenyl]methoxy]methyl]-1,3-dihydro-N,N-dimethyl-;
[1,1'-biphenyl]-4-carbonitrile, 3'-[[[1-[2-(dimethylamino)ethyl]-1,3-dihydro-1-isobenzofuranyl]methoxy]methyl]-5'-(trifluoromethyl)-;
1-isobenzofuranethanamine, 1,3-dihydro-N,N-dimethyl-1-[[[3-(4-pyridinyl)-5-(trifluoromethyl)phenyl]methoxy]methyl]-;
1-isobenzofuranethanamine, 1,3-dihydro-N,N-dimethyl-1-[[[3-(4-morpholinyl)-5-(trifluoromethyl)phenyl]methoxy]methyl]-;
1-isobenzofuranethanamine, 1,3-dihydro-1-[[[3-(4-pyridinyl)-5-(trifluoromethyl)phenyl]methoxy]methyl]-;
1-isobenzofuranethanamine, 1,3-dihydro-1-[[[3-(4-morpholinyl)-5-(trifluoromethyl)phenyl]methoxy]methyl];
1-isobenzofuranethanamine, 1-[[1-[3-bromo-5-(trifluoromethyl)phenyl]ethoxy]methyl]-1,3-dihydro-N,N-dimethyl-;
1-isobenzofuranethanamine, 1-[[1-[3-bromo-5-(trifluoromethyl)phenyl]ethoxy]methyl]-1,3-dihydro-;
1-isobenzofuranethanamine, 1-[[1-[3,5-bis(trifluoromethyl)phenyl]ethoxy]methyl]-1,3-dihydro-N,N-dimethyl-;
1-isobenzofuranethanamine, 1-[[1-[3,5-bis(trifluoromethyl)phenyl]ethoxy]methyl]-1,3-dihydro;
[1,1'-biphenyl]-3-carbonitrile, 3'-[[[1-(2-aminoethyl)-1,3-dihydro-1-isobenzofuranyl]methoxy]methyl]-5'-(trifluoromethyl)-;
[1,1'-biphenyl]-2-carboxamide, 3'-[[[1-(2-aminoethyl)-1,3-dihydro-1-isobenzofuranyl]methoxy]methyl]-5'-(trifluoromethyl)-;
[1,1'-biphenyl]-2-carbonitrile, 3'-[[[1-(2-aminoethyl)-1,3-dihydro-1-isobenzofuranyl]methoxy]methyl]-5'-(trifluoromethyl)-;
1-isobenzofuranethanamine, 1,3-dihydro-1-[[[4'-methoxy-5-(trifluoromethyl) [1,1'-biphenyl]-3-yl]methoxy]methyl]-;
1-isobenzofuranethanamine, 1-[[[4'-chloro-5-(trifluoromethyl)[1,1'-biphenyl]-3-yl]methoxy]methyl]-1,3-dihydro-;
1-isobenzofuranethanamine, 1-[[[4'-fluoro-5-(trifluoromethyl)[1,1'-biphenyl]-3-yl]methoxy]methyl]-1,3-dihydro-;
1-isobenzofuranethanamine, 1-[[[3'-fluoro-5-(trifluoromethyl)[1,1'-biphenyl]-3-yl]methoxy]methyl]-1,3-dihydro-;
1-isobenzofuranethanamine, 1-[[[3'-fluoro-4'-methoxy-5-(trifluoromethyl) [1,1'-biphenyl]-3-yl]methoxy]methyl]-1,3-dihydro-;
1-isobenzofuranethanamine, 1-[[[3'-chloro-5-(trifluoromethyl) [1,1'-biphenyl]-3-yl]methoxy]methyl]-1,3-dihydro-;
1-isobenzofuranethanamine, 1-[[[2'-chloro-5-(trifluoromethyl)[1,1'-biphenyl]-3-yl]methoxy]methyl]-1,3-dihydro-;

1-isobenzofuranethanamine, 1-[[[2',4'-difluoro-5-(trifluoromethyl)[1,1'-biphenyl]-3-yl]methoxy]methyl]-1,3-dihydro-;

1-isobenzofuranethanamine, 1-[[(3-bromo-5-chlorophenyl)methoxy]methyl]-1,3-dihydro-N,N-dimethyl-;

1-isobenzofuranethanamine, 1-[[(3-bromo-5-chlorophenyl)methoxy]methyl]-1,3-dihydro-;

[1,1'-biphenyl]-4-carbonitrile, 3'-chloro-5'-[[[1-[2-(dimethylamino)ethyl]-1,3-dihydro-1-isobenzofuranyl]methoxy]methyl]-;

[1,1'-biphenyl]-4-carbonitrile, 3'-[[[1-(2-aminoethyl)-1,3-dihydro-1-isobenzofuranyl]methoxy]methyl]-5'-chloro-;

1H-2-benzopyran-1-ethanamine, 1-[[[3,5-bis(trifluoromethyl)phenyl]methoxy]methyl]-3,4-dihydro-; and 1H-2-benzopyran-1-ethanamine, 1-[[[3,5-bis(trifluoromethyl)phenyl]methoxy]methyl]-3,4-dihydro-N,N-dimethyl-;

or a pharmaceutically acceptable salt thereof.

12. A composition comprising a pharmaceutically acceptable amount of a compound of claim 1 and a pharmaceutically acceptable carrier.

13. A method for treating a disorder associated with aberrant levels of tachykinins or serotonin comprising administering an effective amount of a compound of claim 1 to a patient afflicted with the disorder.

14. The method of claim 13 where the disorder is anxiety.

15. The method of claim 13 where the disorder is depression, obsessive compulsive disorder, bulimia, or panic disorder.

* * * * *

UNITED STATES PATENT AND TRADEMARK OFFICE
CERTIFICATE OF CORRECTION

PATENT NO. : 7,632,861 B2  Page 1 of 1
APPLICATION NO. : 12/266627
DATED : December 15, 2009
INVENTOR(S) : Joanne J. Bronson et al.

It is certified that error appears in the above-identified patent and that said Letters Patent is hereby corrected as shown below:

In the Claims:

Claim 8:

Column 63, line 32, change "$NR^7R^5$" to -- $NR^7R^8$ --.

Claim 11:

Column 64, line 6, change ":" to -- ; --.

Signed and Sealed this

Twenty-fifth Day of October, 2011

David J. Kappos
*Director of the United States Patent and Trademark Office*